United States Patent
Hanna et al.

(10) Patent No.: US 11,319,311 B2
(45) Date of Patent: May 3, 2022

(54) CRYSTALLINE FORMS OF ACTINOMYCIN D FOR TREATMENT OF CANCER

(71) Applicant: TRANSGENEX NANOBIOTECH, INC., Tampa, FL (US)

(72) Inventors: Mazen Hanna, Tampa, FL (US); Manomi Perera, Tampa, FL (US); Jiyu Yan, Tampa, FL (US); Andrew Hanna, Lutz, FL (US)

(73) Assignee: TRANSGENEX NANOBIOTECH, INC., Tampa, FL (US)

( * ) Notice: Subject to any disclaimer, the term of this patent is extended or adjusted under 35 U.S.C. 154(b) by 83 days.

(21) Appl. No.: 16/969,262

(22) PCT Filed: Feb. 11, 2019

(86) PCT No.: PCT/US2019/017474
§ 371 (c)(1),
(2) Date: Aug. 12, 2020

(87) PCT Pub. No.: WO2019/160805
PCT Pub. Date: Aug. 22, 2019

(65) Prior Publication Data
US 2021/0053963 A1      Feb. 25, 2021

Related U.S. Application Data

(60) Provisional application No. 62/629,895, filed on Feb. 13, 2018.

(51) Int. Cl.
*C07D 413/14* (2006.01)
*A61K 9/00* (2006.01)

(52) U.S. Cl.
CPC .......... *C07D 413/14* (2013.01); *A61K 9/0014* (2013.01); *A61K 9/0019* (2013.01); *C07B 2200/13* (2013.01)

(58) Field of Classification Search
CPC ................ A61K 9/0014; A61K 9/0019; C07B 2200/13; C07C 31/04; C07C 323/58; C07C 69/84; C07C 69/94; C07C 201/00; C07D 413/14; C07D 519/00; A61P 31/04
See application file for complete search history.

(56) References Cited

U.S. PATENT DOCUMENTS

| 2,378,449 A | 6/1945 | Tishler |
| 2,953,495 A | 9/1960 | Brockmann et al. |
| 3,282,787 A | 11/1966 | Gaeumann et al. |
| 2005/0181041 A1 | 8/2005 | Goldman |

FOREIGN PATENT DOCUMENTS

WO      2004/078161 A1      9/2004

OTHER PUBLICATIONS

Sobell et al., Nature New biology vol. 2321, Jun. 16, 1971 (Year: 1971).*
International Search Report and Written Opinion in International Application No. PCT/US2019/017474, dated Apr. 12, 2019.

* cited by examiner

*Primary Examiner* — Jean P Cornet
(74) *Attorney, Agent, or Firm* — J.A. Lindeman & Co. PLLC

(57) ABSTRACT

Synthesis and characterization of novel DACT forms suitable for pharmaceutical compositions in drug delivery systems to treat cancer in humans or a warm-blooded mammals. The novel forms include but not limited to cocrystals, salts, solvates of salts, and mixtures thereof.

20 Claims, 16 Drawing Sheets

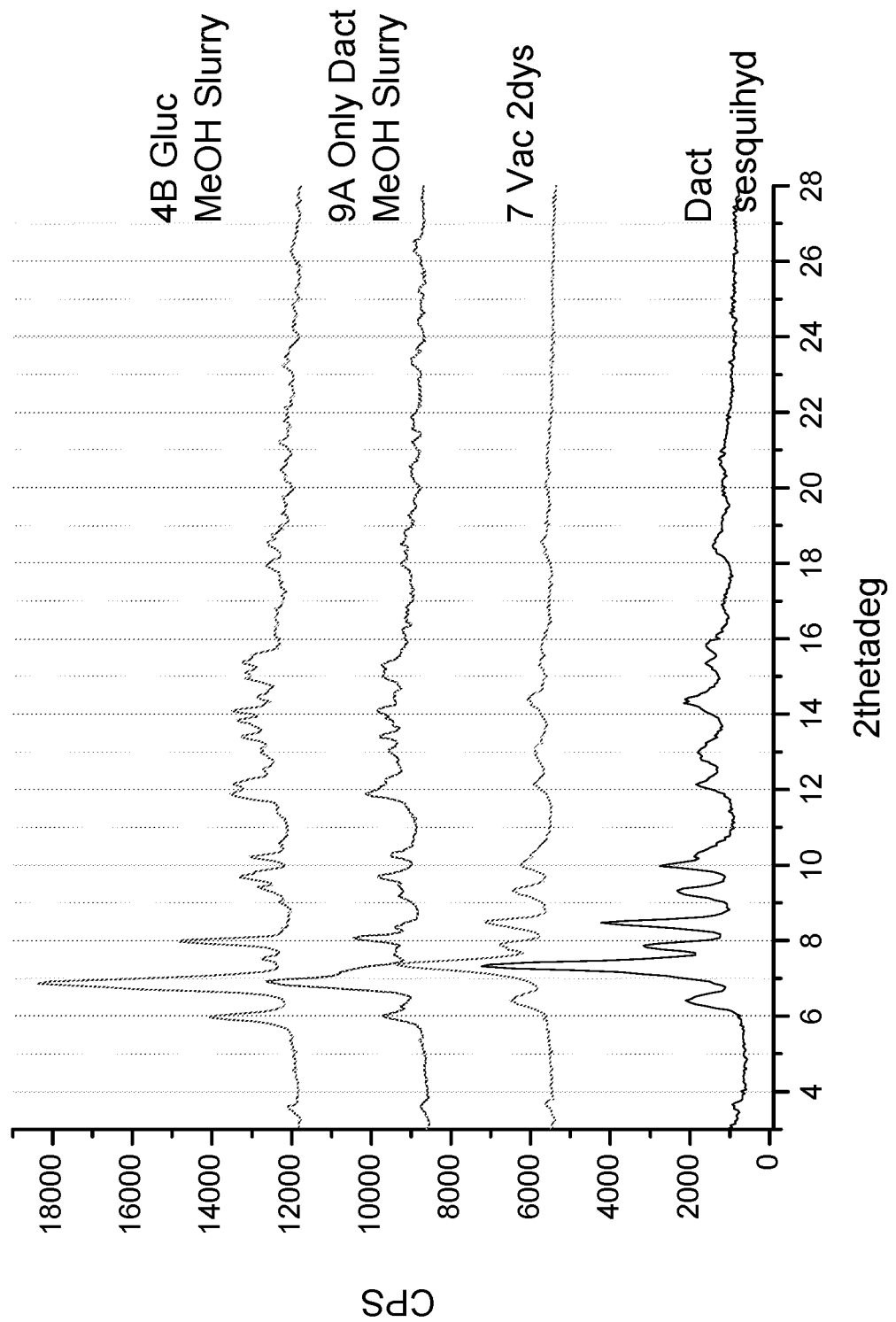
Figure 1. DACT methanolate PXRD profiles

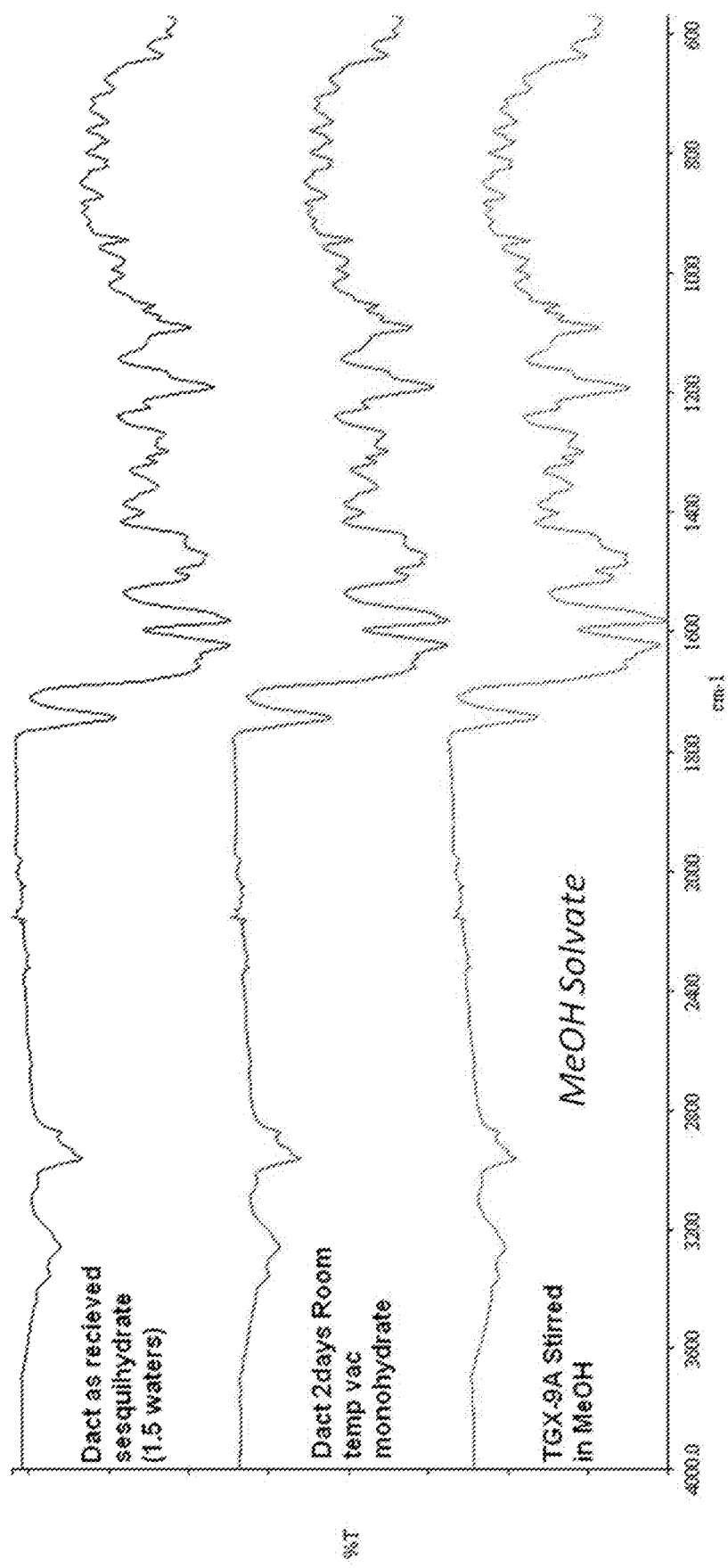
Figure 2. DACT methanolate FTIR spectrum (bottom spectrum)

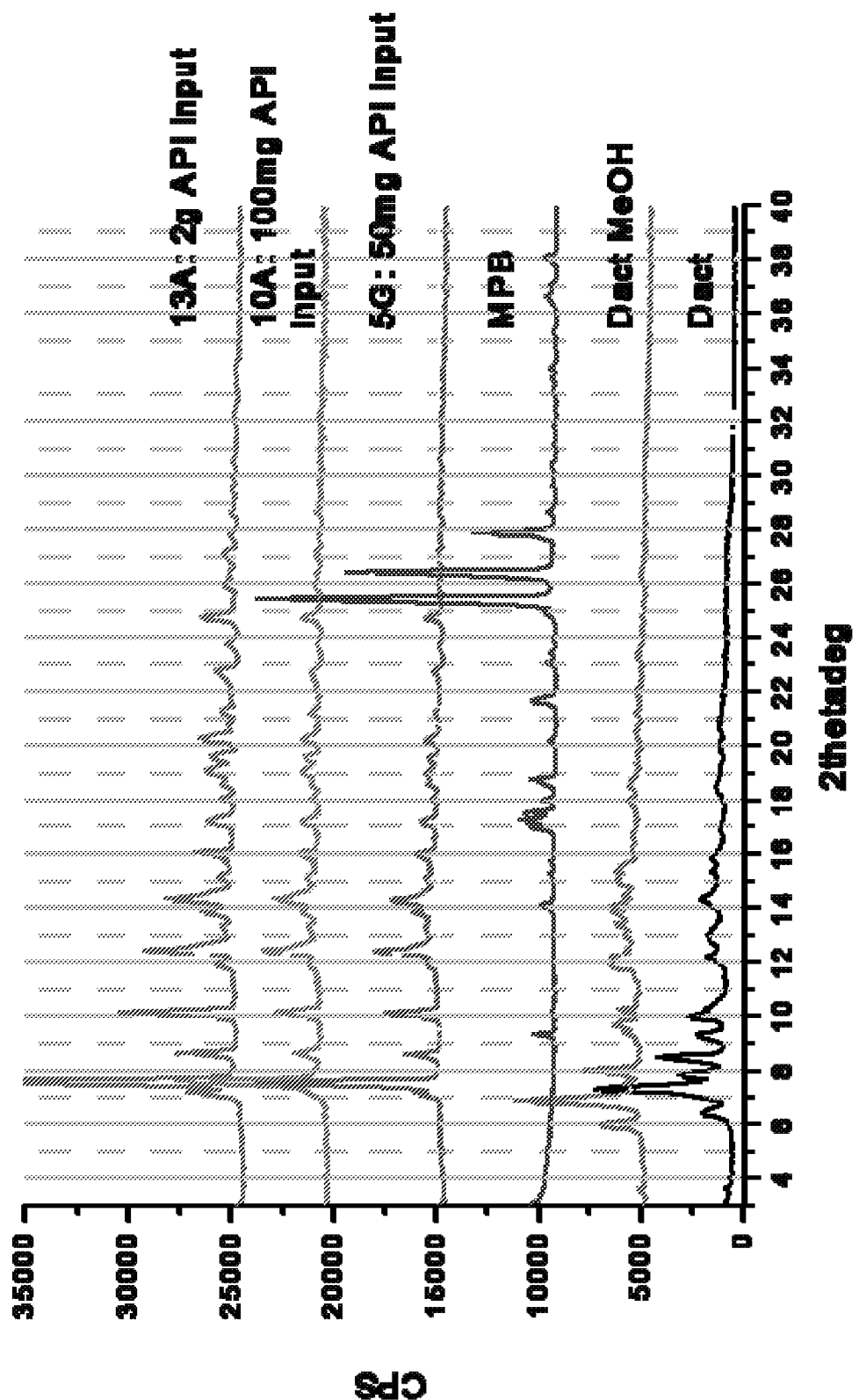
Figure 3. DACT:methylparaben PXRD profiles

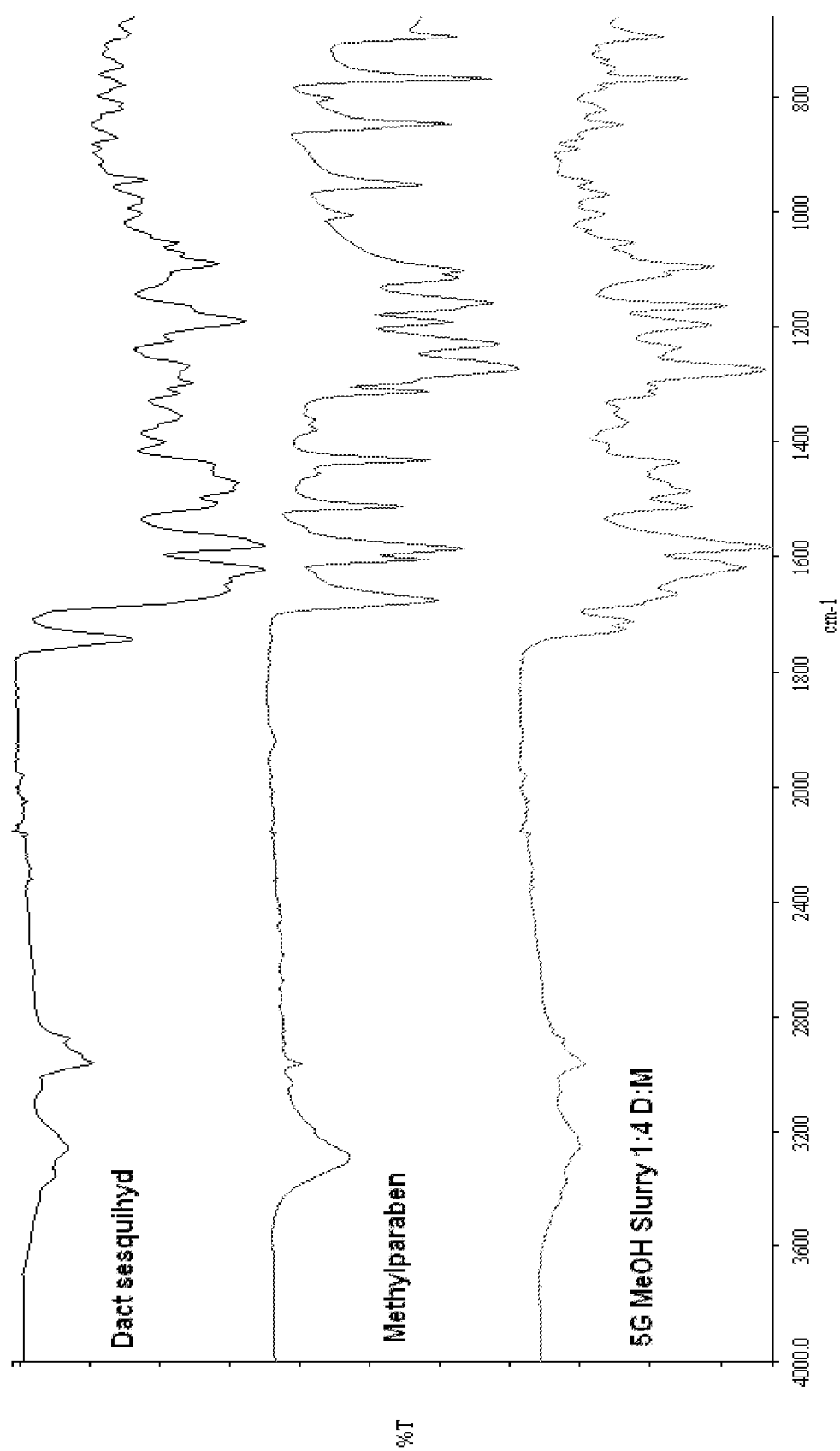
Figure 4. DACT:methylparaben FTIR spectrum (bottom spectrum)

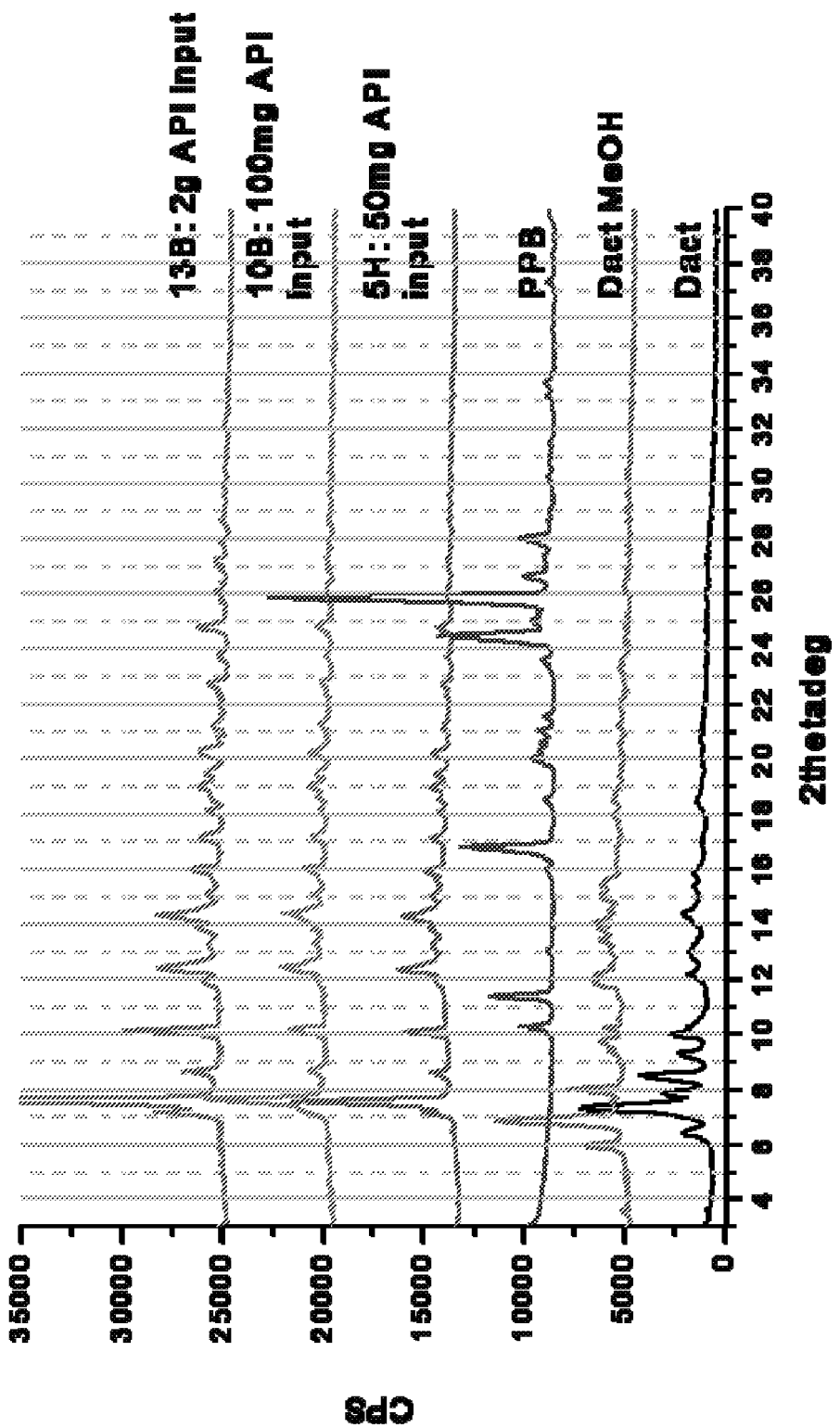
Figure 5. DACT:propylparaben PXRD profiles

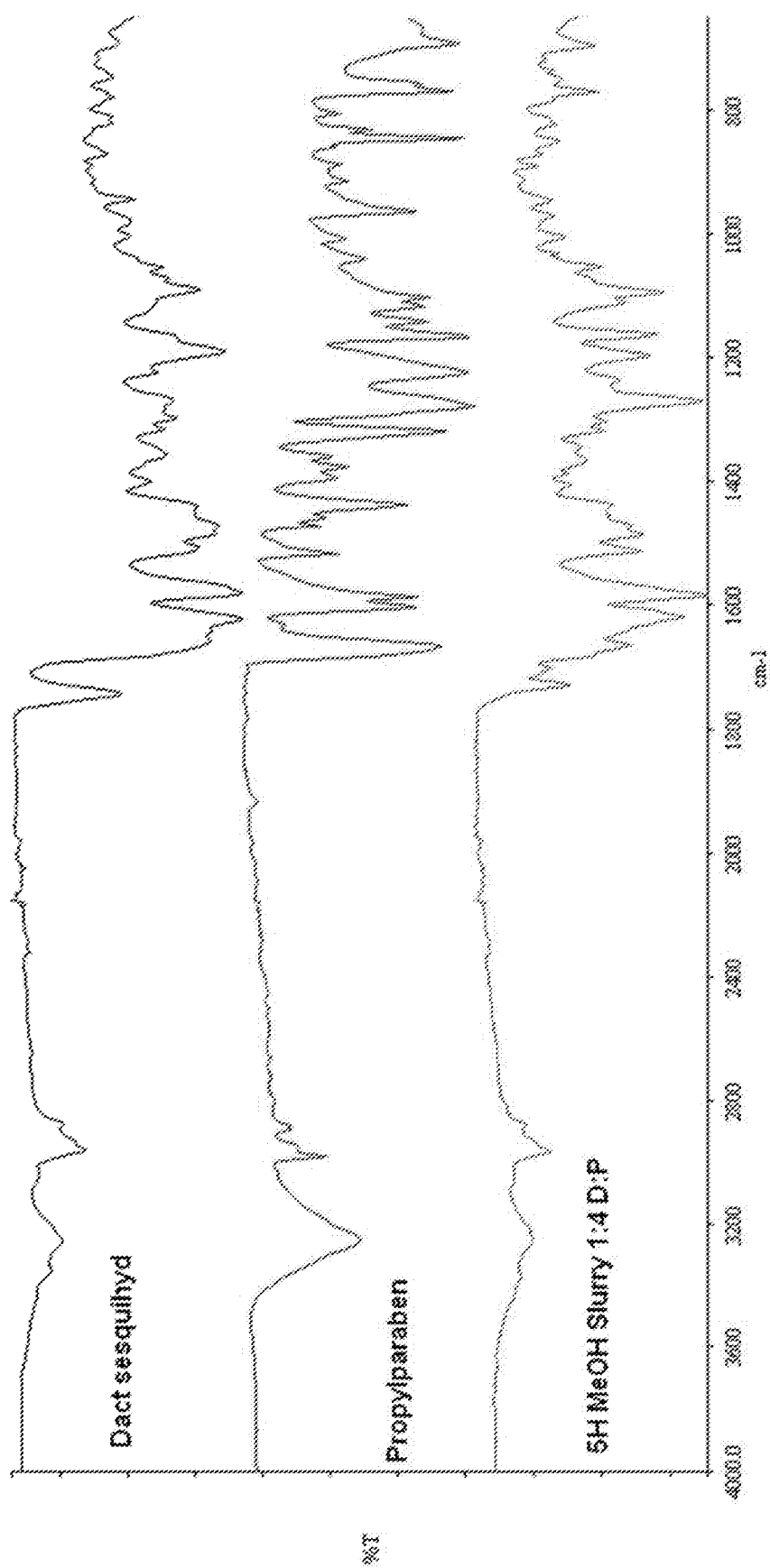
Figure 6. DACT:propylparaben FTIR spectrum (bottom spectrum)

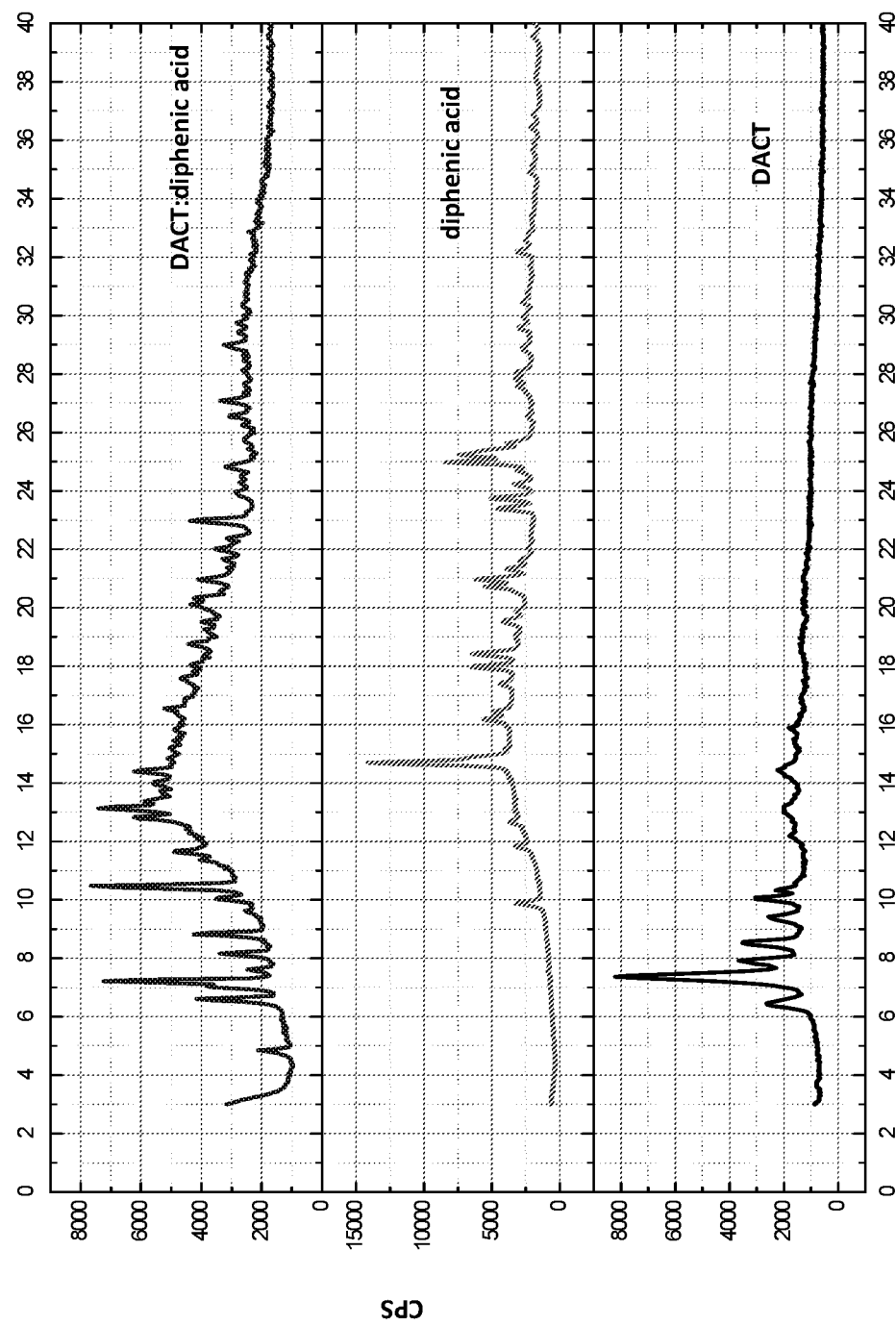
Figure 7. DACT:diphenic acid PXRD profiles

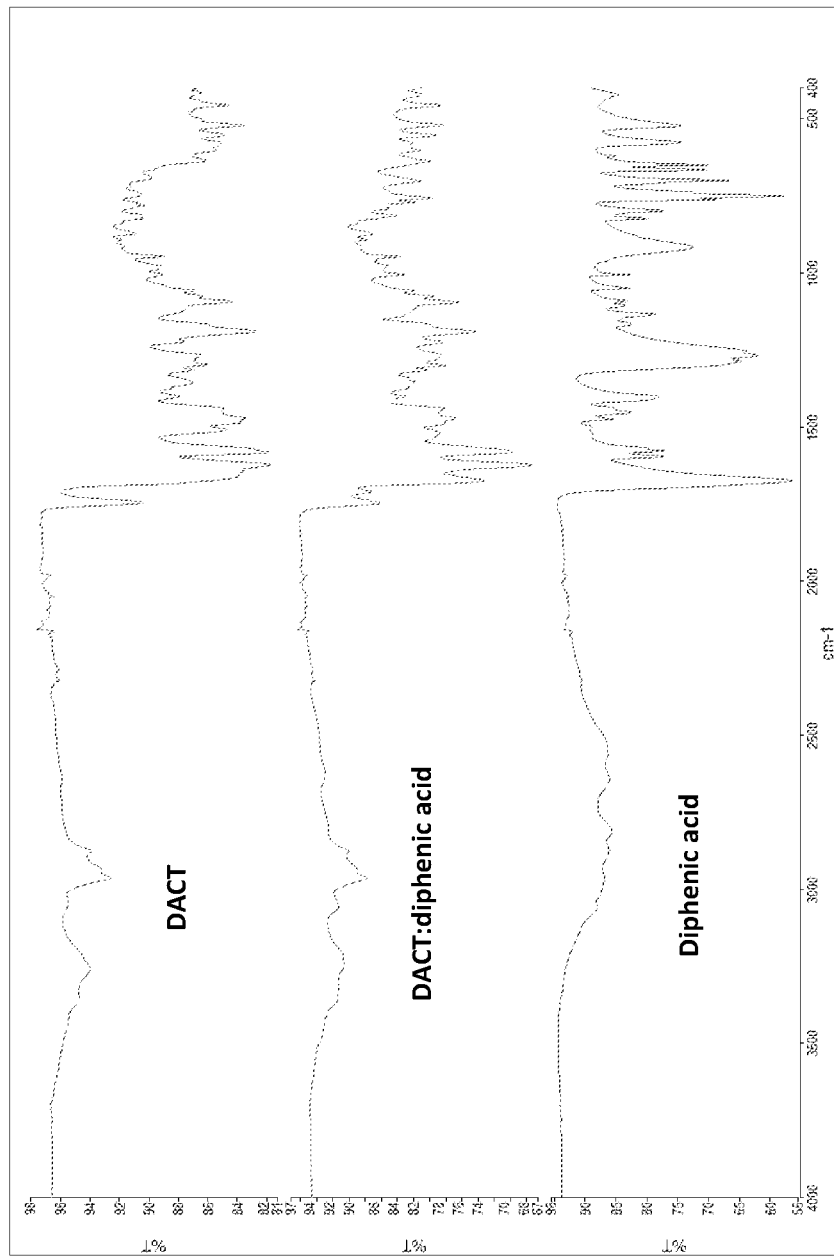
Figure 8. DACT:diphenic acid FTIR spectrum

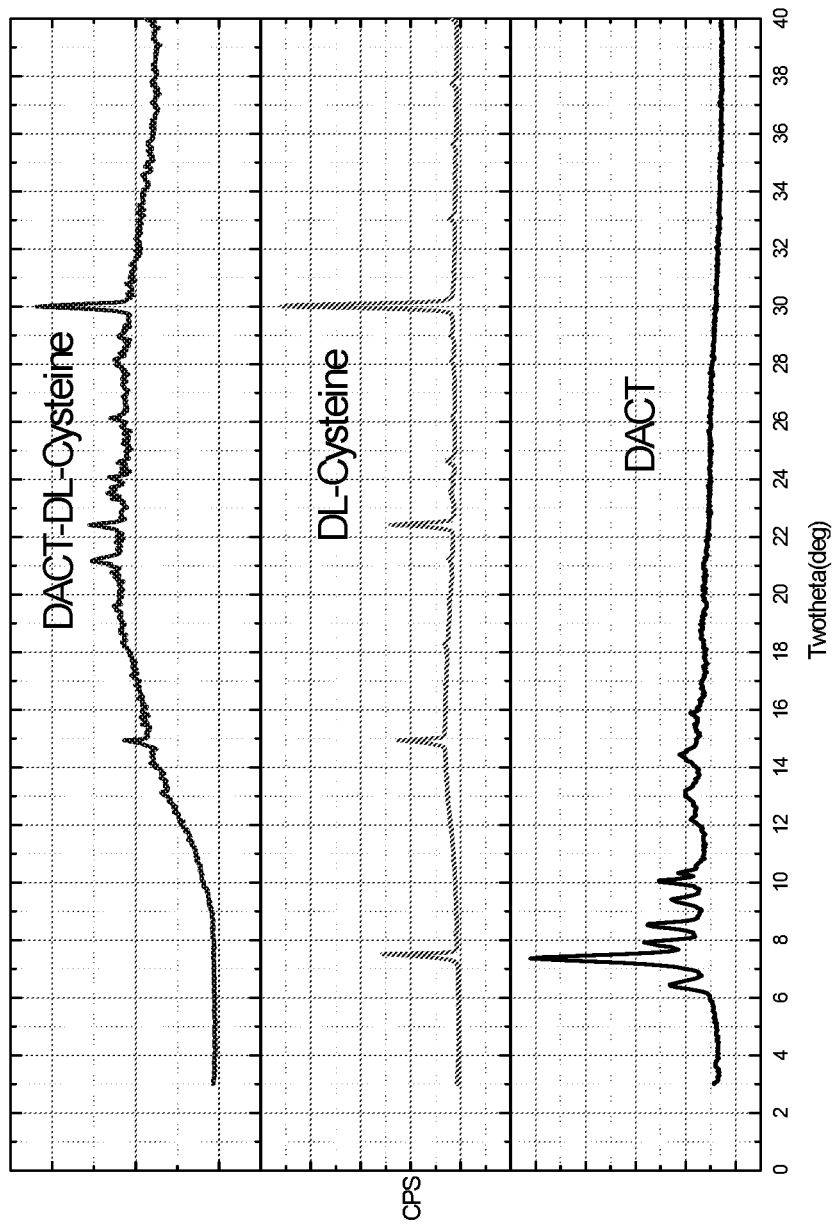
Figure 9. PXRD profiles of DACT:DL-cysteine

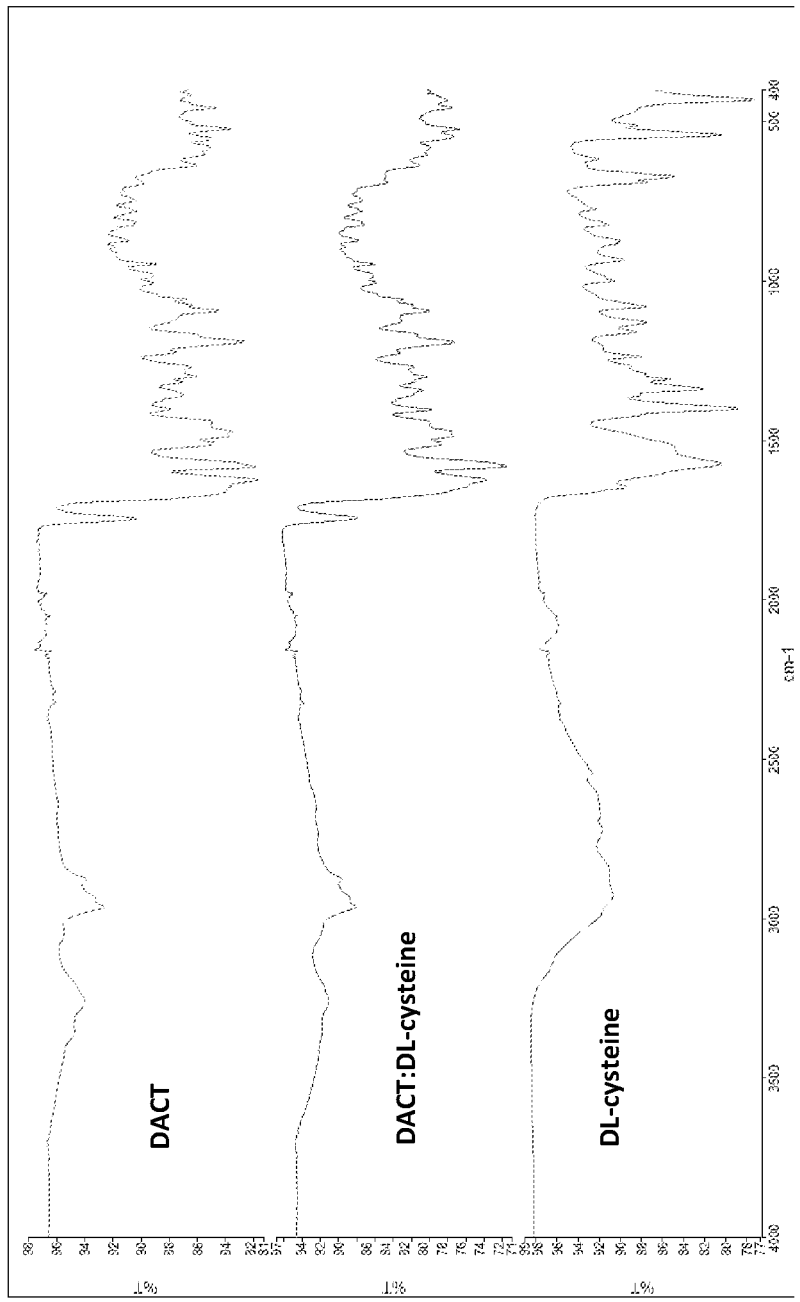
Figure 10. DACT:DL-cysteine FTIR spectrum

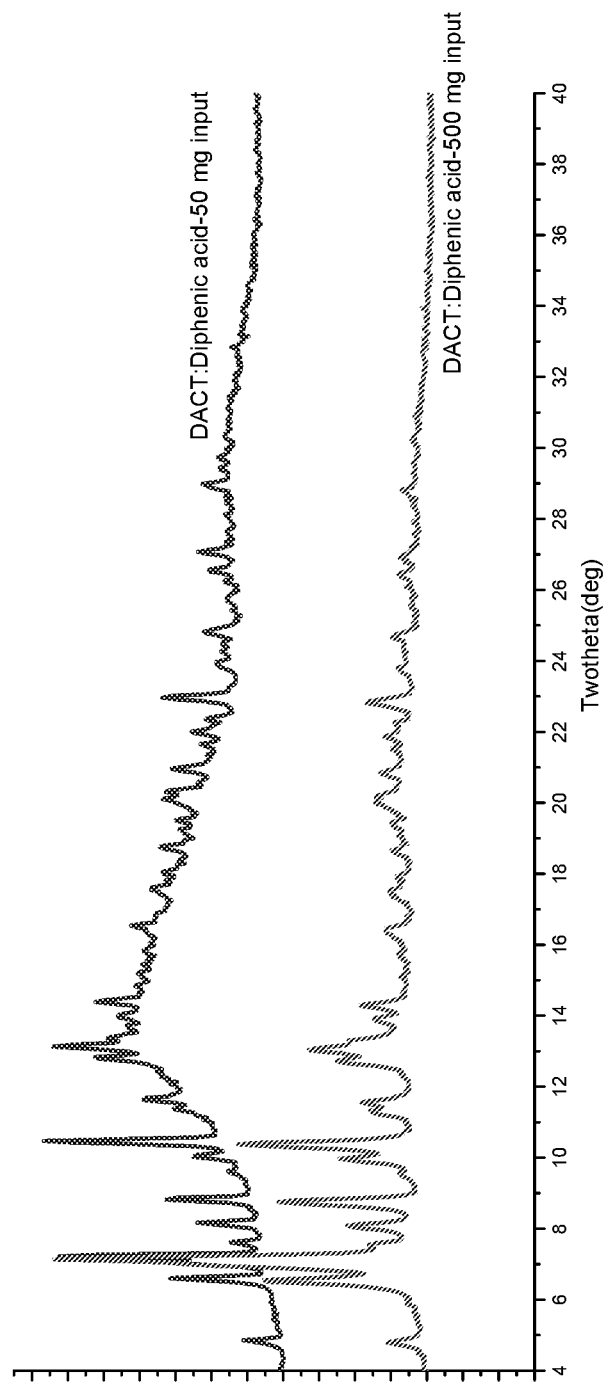
Figure 11. PXRD diffractogram of DACT:diphenic acid scaled up product

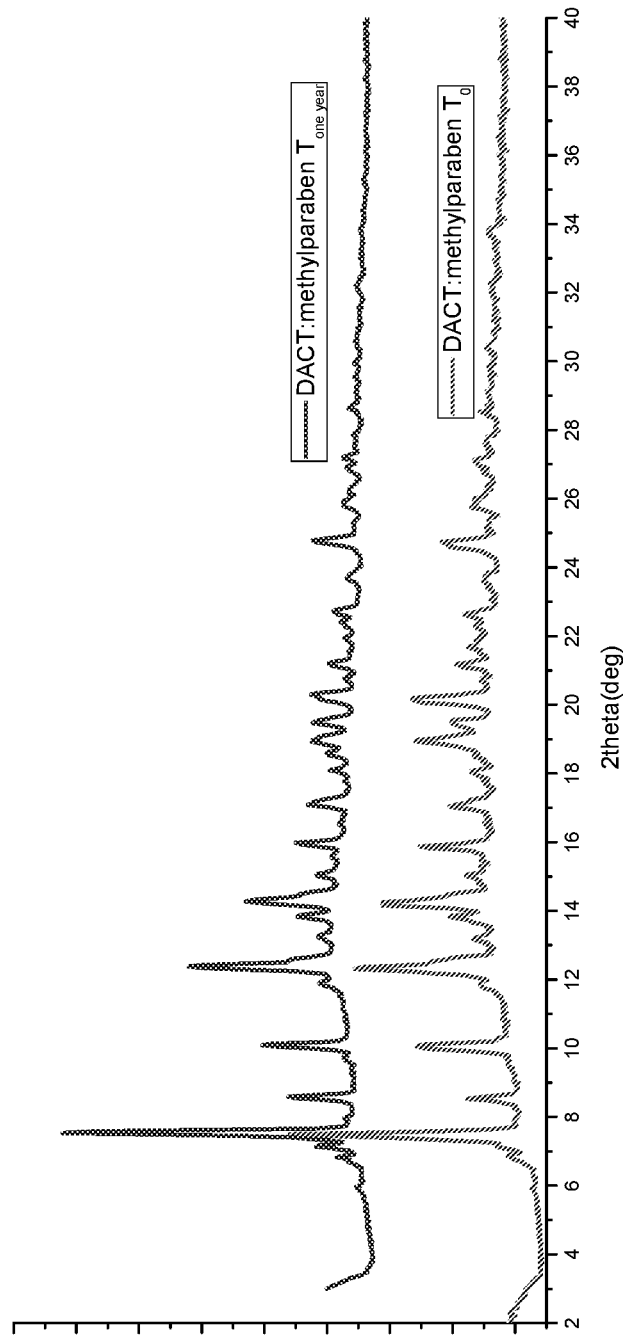
Figure 12. PXRD analysis of DACT:methylparaben after one year of stability testing

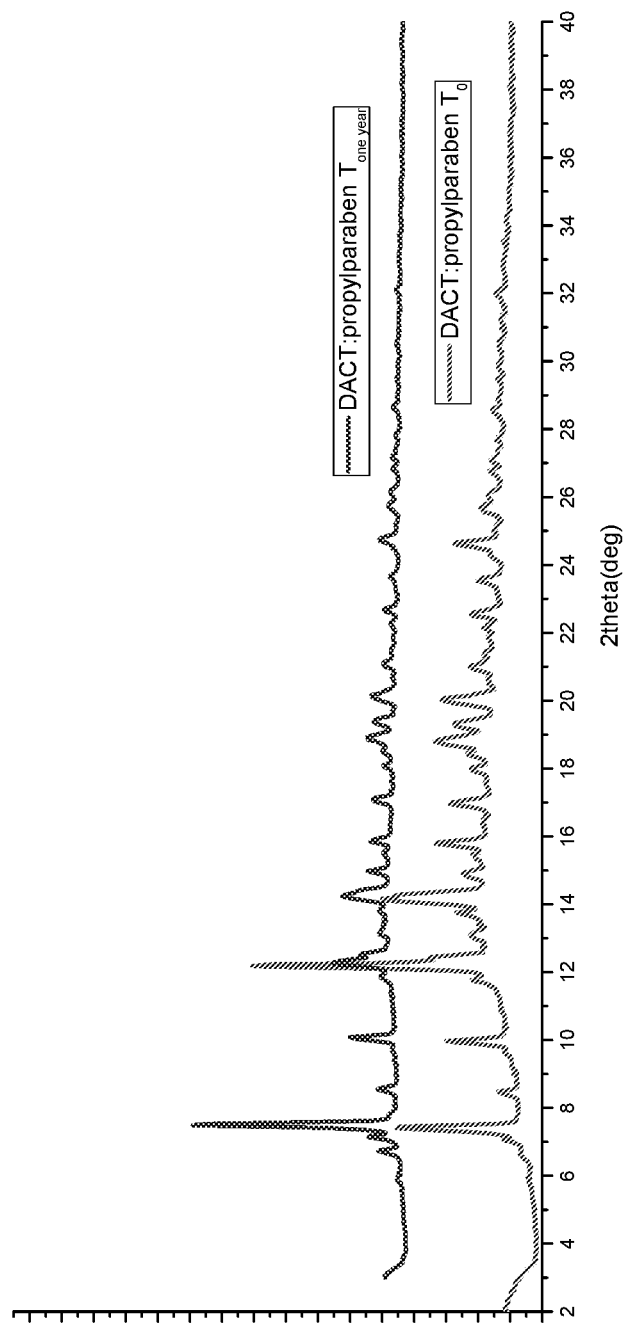
Figure 13. PXRD diffractogram of DACT:propylparaben after one year of stability testing

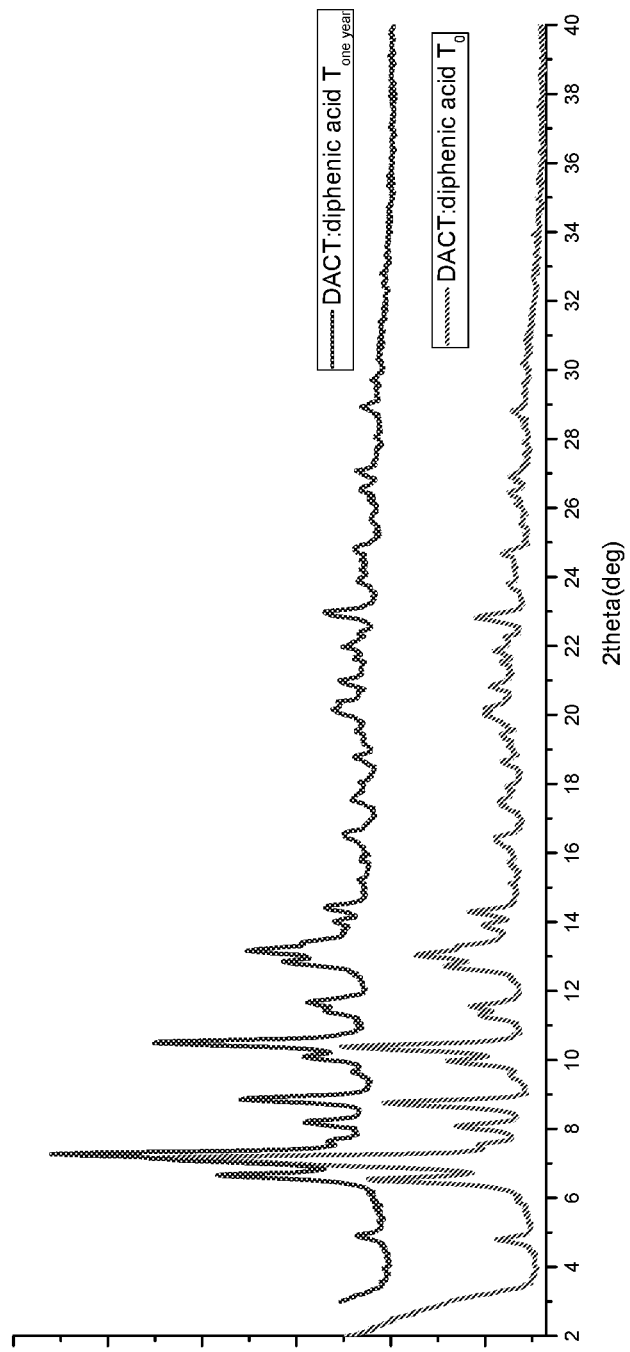
Figure 14. PXRD analysis of DACT:diphenic acid after one year of stability testing

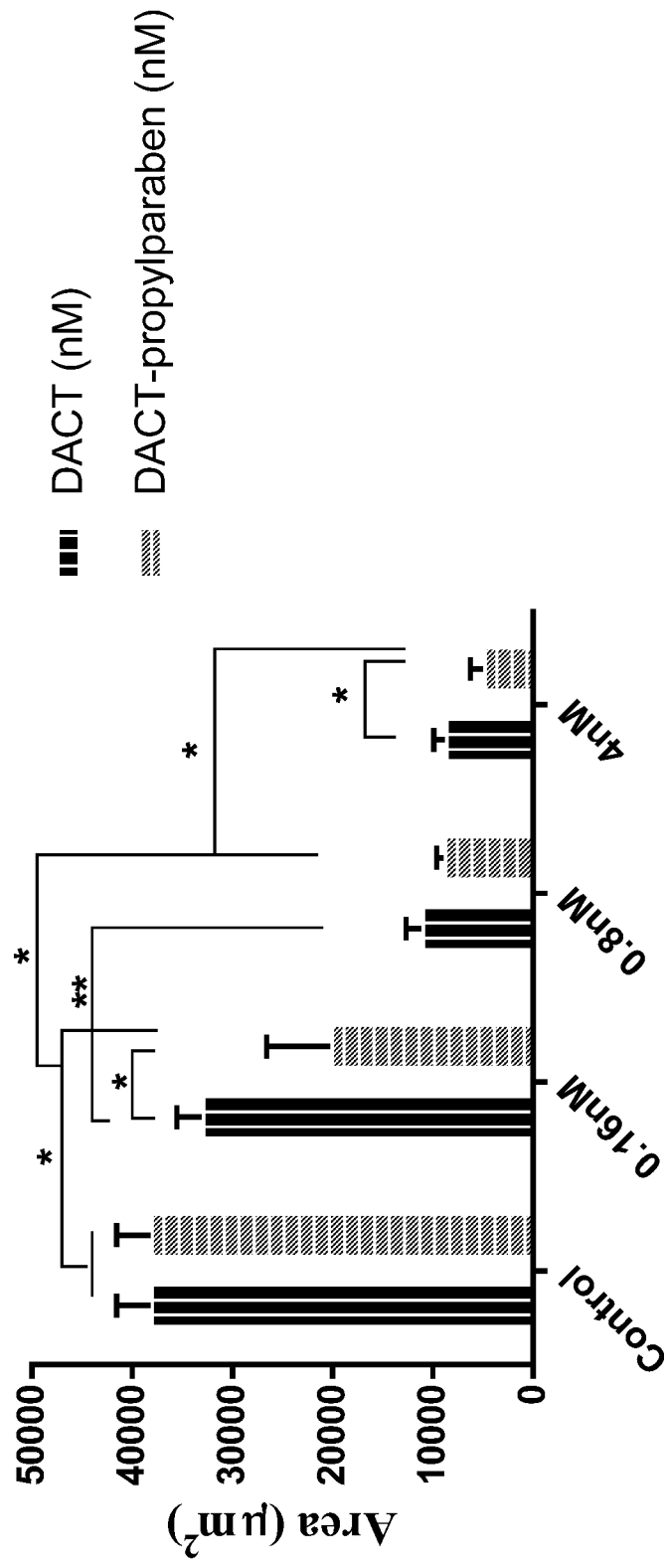

Figure 15. Sphere image area for the sarcoma cell line SK-ES-1 cells. The data indicates the cells treated with molecular complex DACT:propylparaben has less of total sphere image area than that with pure DACT. The sphere image area was calculated based on the sum area of spheres with diameter over 50 μm in each treatment well. * $P < 0.05$, ** $P < 0.001$ using the unpaired Student's t tests.

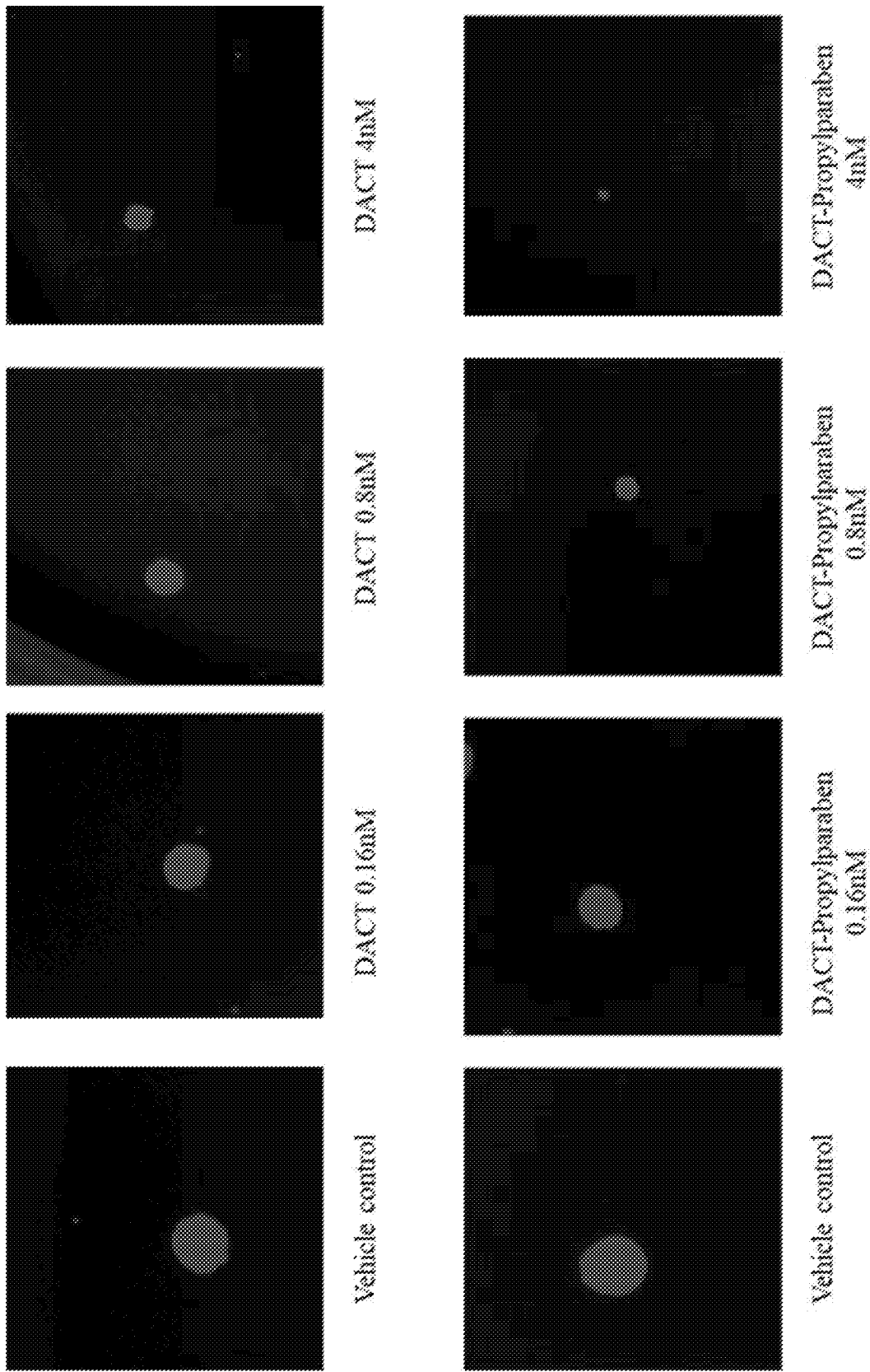
Figure 16. Images of SK-ES-1 cell spheres on day 6 of seeding (in blue color) at different concentrations of DACT:propylparaben

CRYSTALLINE FORMS OF ACTINOMYCIN D FOR TREATMENT OF CANCER

CROSS-REFERENCE TO RELATED APPLICATIONS

This application claims priority to U.S. Provisional Application No. 62/629,895, filed Feb. 13, 2018, which is incorporated herein by reference.

FIELD OF THE INVENTION

This disclosure pertains to generating novel crystalline forms of Actinomycin D for the safe and effective inhibition of cancer stem cells and treatment of a variety of cancers in including and particularly drug- and radio-resistant cancers. The novel forms include but not limited to cocrystals, salts, solvates of salts, and mixtures thereof. Methods for the preparation of and pharmaceutical compositions suitable for drug delivery systems that include one or more of these new forms are also disclosed.

BACKGROUND OF THE INVENTION

Cancers continue to constitute a major cause of morbidity and mortality worldwide. Traditional therapies often cannot completely eradicate tumors, prevent cancer recurrence, or prevent metastasis in cancer patients. Recently, in some cases, these failures in effectively treating cancers have been attributed to cancer stem cells (CSCs), which have properties of self-renewal, tumor initiation, and tumor maintenance, and are considered a major cause of mortality after relapse following treatment.

While chemotherapy and other conventional cancer therapies may be more effective at killing bulk tumor cells, CSCs may manage to escape and seed new tumor growth, due to the survival of quiescent CSCs [Clarke et al. (2006) *Cancer Res.* 66:9339-44; Reya et al. (2001) *Nature* 414:105-11]. There is growing evidence supporting the role of CSCs in tumorigenesis [Gupta et al. (2009) *Nat. Med.* 15:1010-12], tumor heterogeneity [Meacham et al. (2013) *Nature* 501: 328-37], resistance to chemotherapeutic and radiation therapies [Li et al. (2008) *J. Natl. Cancer Inst.* 100:672-9; Diehn et al. (2009) *Nature* 458:780-3], and the metastatic phenotype [Shiozawa et al. (2013) *Pharmacol. Ther.* 138:285-93]. Therefore, the development of specific therapies that target and inhibit CSCs holds promise for improving the survival and quality of life for cancer patients, especially those with metastatic disease [Takebe et al. (2011) *Nat. Rev. Clin. Oncol.* 8:97-106; Dalerba et al. (2007) *Cell Stem Cell* 1:241-42].

Particularly, there is an urgent need for therapeutic agents that target CSCs self-renewal, regeneration, and differentiation processes. These agents, such as small molecules or biologics, should be designed to target CSCs, CSC-related biomarkers, and CSC pathways that affect fundamental processes associated with carcinogenesis, tumor progression, maintenance, metastasis drug resistance, and cancer recurrence.

Actinomycin D also known as Dactinomycin, ActD, or DACT is one of a group of antibiotics produced by various species of *Streptomyces*. Among different species of *Streptomyces*, only *Streptomyces* parvullus yields an essentially pure DACT substance that contains only traces of similar compounds differing in the amino acid content of the peptide side chains. The empirical formula is $C_{62}H_{86}N_{12}O_{16}$, IUPAC name as 2-amino-4,6-dimethyl-3-oxo-3H-phenoxazine-1,9-dicarboxylic acid bis-[(5,12-diisopropyl-9,13,16-trimethyl-4,7,11,14,17-pentaoxo-hexadecahydro-10-oxa-3a,6,13,16-tetraaza-cyclopentacyclohexadecen-8-yl)-amide, and the structural formula, which basically is two cyclic peptides attached to a phenoxazine:

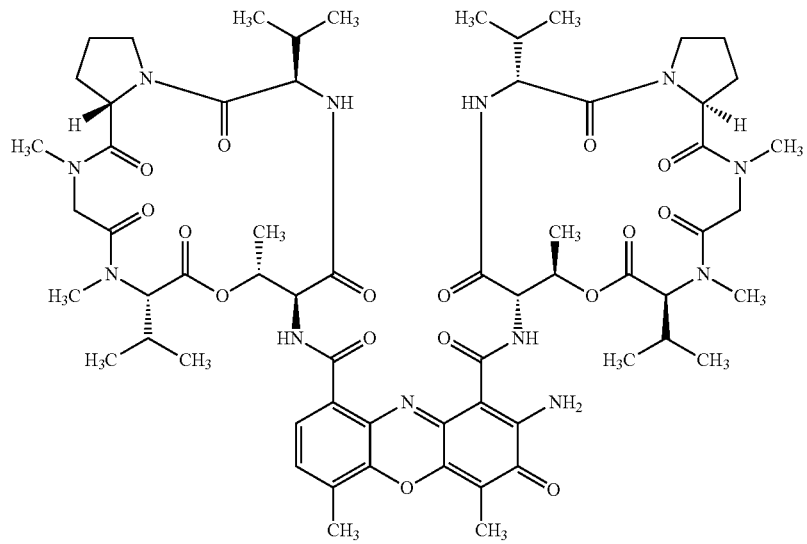

DACT has been known for more than 70 years. It was first isolated by Selman Waksman in 1940. [Waksman et al. (1940] "Bacteriostatic and bacteriocidal substances produced by soil actinomycetes," *Proc Soc Exper Biol.* 45:609-14]. Additionally, it was the first antibiotic shown to have anti-cancer activity [Hollstein (1974) "Actinomycin. Chemistry and mechanism of action," *Chemical Reviews* 74(6): 625-52]. More specifically, it binds to DNA and inhibits RNA synthesis (transcription), with chain elongation more sensitive than initiation, termination, or release. Due to the impaired mRNA production, protein synthesis also declines after DACT therapy [American Medical Association; Drug Evaluations Annual, 1993, p2015].

DACT was first approved by the FDA on Dec. 10, 1964 and launched by Merck Sharp and Dohme under the trade name Cosmegen. It is supplied as a sterile, yellow, amorphous powder with 0.5 mg dose for IV use with a drug black box warning of "Highly Toxic." It has been used to treat cancers such as gestational trophoblastic neoplasia, Wilms' tumor, rhabdomyosarcoma, Ewing's sarcoma, malignant hydatid form mole. It can also be combined with other drugs in chemotherapy regimens, like the VAC regimen with vincristine and cyclophosphamide for treating rhabdomyosarcoma and Ewing's sarcoma.

DACT is poorly absorbed from the GI tract. The drug is extremely irritating to tissues and is, therefore, administered IV [American Society of Health System Pharmacists; AHFS Drug Information 2009. Bethesda, Md. (2009), p. 1025].

Scant literature is available on manipulation of the solid form of DACT. Crystalline forms of ethanoate/hydrate and various hydrates including an undecanoate and dodecanoate are published in the Cambridge Structural Database (CSD February 2017 Update) [see Sobell et al. (1971) Nature 231:200; Jain et al. (1972) J Mol. Biol. 68:P1]. Complexes with DNA segments are also published in CSD represented by the following DNA sequences, (ACGTAGCTACGT)2: [actinomycin D, (echinomycin)2] and d(ACGTAGC-TACGT)2:[actinomycin D, (triostin A)2] [Takusagawa et al. (2000) Acta Cryst D Biol Crystalogr. 56(3)]. Stability has been an issue during the manufacturing and storage of DACT. We reason that a deliberate molecular design approach can be used to create a molecular complex of DACT (i.e., DACT and a cocrystal former) in a single crystalline structure, could improve its stability. Additionally, rather than mixing the cocrystal former and DACT as a physical mix or blend, such molecular design and single crystal structure might lead to the elimination of all the batch to batch blend uniformity and particle segregation problems that powder blends often suffer from. It also simplifies the manufacture of the solid dosage form that is made of a drug and excipient to a degree that the final solid dosage form is basically the powder of the molecular complex by design.

Furthermore, this molecular complex will have very different physicochemical properties than that of the parent drug and co-former derived therefrom. Such properties include melting point, thermal and electrical conductivity, aqueous solubility, rate of aqueous dissolution, and potentially permeability. The new forms are also considered useful to create oral dosage forms and injectables that mitigate its soft tissue toxicity. The upward trend in the use of oral drugs continues with the goal to decrease the overall cost of healthcare. Thus, there is an opportunity to create oral dosage forms of IV drugs where oral dosage forms do not yet exist due to their poor aqueous solubility and/or poor permeability and in this case soft tissue toxicity, providing a clear clinical benefit for patients.

SUMMARY OF THE INVENTION

The present disclosure is directed towards generating new forms of DACT that have improved physicochemical characteristics. One aspect of the present disclosure includes novel molecular complexes of DACT neutral and ionic that includes cocrystals, salts, and solvates (e.g., hydrates and mixed solvates as well as solvates of salts), and mixtures containing such materials. In addition, the disclosure further includes methods for the preparation of such complexes.

The disclosure further includes compositions of molecular complexes of DACT suitable for incorporation in a pharmaceutical dosage form. Specific molecular complexes pertaining to the disclosure include, but are not limited to, cocrystals of DACT and methyl- and propyl-parabens, cysteine, diphenic acid, and DACT methanol solvates. Obvious variants of the disclosed DACT forms in the text, including those described by the drawings and examples will be readily apparent to the person of ordinary skill in the art having the present disclosure, and such variants are considered to be a part of the current invention.

The disclosure also includes results of characterization of the new molecular complexes by PXRD and FTIR confirming their novelty compared with that of their parent molecule and the coformer.

The foregoing and other features and advantages of the disclosed technology will become more apparent from the following detailed description, which proceeds with reference to the accompanying drawings. Such description is meant to be illustrative, but not limiting, of the invention.

BRIEF DESCRIPTION OF THE DRAWINGS

FIG. 1. PXRD profiles of DACT methanolate novel form. 4B is DACT:methanol solvate obtained from a DACT methanol slurry in the presence of glucose; 9A is DACT: methanol solvate obtained from a slurry of DACT and methanol; 7 is DACT powder starting material under 2 days of vacuum; and DACT Sesquehydrate is the starting material.

FIG. 2. FTIR spectrum of DACT methanolate novel form.

FIG. 3. PXRD profiles of DACT:methylparaben novel form. 13A is DACT:methylparaben cocrystal obtained from 2 g DACT input; 10A is DACT:methylparaben cocrystal obtained from 100 mg DACT input; 5G is DACT:methylparaben cocrystal obtained from 50 mg DACT input; and MBP is methylparaben, DACT, and DACT methanolate form.

FIG. 4. FTIR spectrum of DACT:methylparaben novel form. Top spectrum is for DACT starting material; middle profile is the DACT:methylparaben novel form; and bottom spectrum is for DACT methanolate form.

FIG. 5. PXRD profiles of DACT:propylparaben novel form at different inputs of DACT starting material. 13B is DACT:propylparaben cocrystal obtained from 2 g DACT input; 10B is DACT:propylparaben cocrystal obtained from 100 mg DACT input; 5H is DACT:propylparaben cocrystal obtained from 50 mg DACT input; PPB is propylparaben; DACT MeOH is methanolate form; and Dact is DACT.

FIG. 6. FTIR spectrum of DACT:propylparaben novel form (middle spectrum).

FIG. 7. PXRD profiles of DACT:diphenic acid novel form (top profile).

FIG. 8. FTIR spectrum of DACT:diphenic acid novel form (middle spectrum).

FIG. 9. PXRD profiles of DACT:DL-cysteine novel form (top profile).

FIG. 10. FTIR spectrum of DACT:DL-cysteine novel form (middle spectrum).

FIG. 11. PXRD diffractogram of DACT:diphenic acid scaled up.

FIG. 12. PXRD diffractogram of DACT:methylparaben after one year of stability testing.

FIG. 13. PXRD profile of DACT:propylparaben after one year of stability testing.

FIG. 14. PXRD profile of DACT:diphenic acid after one year of stability studies.

FIG. 15. Sphere area of sarcoma cells treated with DACT: propylparaben.

FIG. 16. Images of cancer cell spheres on day 6 of seeding (in blue color) at different concentrations of DACT:propylparaben.

DETAILED DESCRIPTION OF THE INVENTION

In general, active pharmaceutical ingredients (APIs) in pharmaceutical compositions can be prepared in a variety of different forms. Such compounds can be prepared to have a variety of different chemical forms including chemical derivatives, solvates, hydrates, cocrystals, and/or salts. Such compounds can also be prepared to have different physical forms. For example, they may be amorphous, may have different crystalline polymorphs, or may exist in different solvated or hydrated states. The discovery of new forms of a pharmaceutically useful compound may provide an opportunity to improve the performance characteristics of a pharmaceutical product. Additionally, it expands the array of resources available for designing, for example, a pharmaceutical dosage form of a drug with a targeted release profile or other desired characteristics.

A specific characteristic that can be targeted includes the crystal form of an API. By altering the crystal form, it therefore becomes possible to vary the physical properties of the target molecule. For example, crystalline polymorphs typically have different aqueous solubility from one another, such that a more thermodynamically stable polymorph is less soluble than a less thermodynamically stable polymorph. In addition to water solubility, pharmaceutical polymorphs can also differ in properties such as rate of dissolution, shelf-life, bioavailability, morphology, vapor pressure, density, color, and compressibility. Accordingly, it is desirable to enhance the properties of an active pharmaceutical compound by forming molecular complexes such as a cocrystal, a salt, a solvate or hydrate with respect to aqueous solubility, rate of dissolution, bioavailability, Cmax, Tmax, physicochemical stability, down-stream processibility (e.g., flowability compressibility, degree of brittleness, particle size manipulation), crystallization of amorphous compounds, decrease in polymorphic form diversity, toxicity, taste, production costs, and manufacturing methods.

During the development of drugs in an oral delivery setting, it is frequently advantageous to have novel crystalline forms of such drug materials that possess improved properties, including increased aqueous solubility and stability. It is also desirable, in general, to increase the dissolution rate of such solid forms and potentially increase their bioavailability. This also applies to the development of novel forms of DACT which, when administered orally to a subject could achieve a greater or similar bioavailability and PK profile when compared to an IV or other formulations on a dose-for-dose basis.

Cocrystals, salts, solvates, and hydrates of DACT of the present invention could give rise to improved properties. For example, a new DACT form for use in oral dosage forms or injectables, including direct injection and infusion, are particularly advantageous. A number of novel DACT forms have been synthesized, characterized, and disclosed herein.

The present invention further includes compositions of molecular complexes of DACT suitable for incorporation in a pharmaceutical dosage form. Specific molecular complexes pertaining to the disclosure include, but are not limited to, complexes of DACT and methanol, DACT and methylparaben, DACT and propylparaben, DACT and diphenic acid, and DACT and DL-cysteine. Obvious variants of the disclosed DACT forms in the disclosure, including those described by the drawings and examples, will be readily apparent to the person of ordinary skill in the art having the present disclosure and such variants are considered to be a part of the current invention.

In one aspect, the invention provides for a crystalline form of DACT and methanol. In one embodiment, the DACT:methanol crystalline form is a solvate.

In one embodiment, the DACT:methanol crystalline form is characterized by a powder X-ray diffraction pattern comprising a powder X-ray diffraction peak at about 6.0° 2θ±0.2° 2θ.

In another embodiment, the DACT:methanol crystalline form is characterized by a powder X-ray diffraction pattern comprising a powder X-ray diffraction peak at about 6.9° 2θ±0.2° 2θ.

In another embodiment, the DACT:methanol crystalline form is characterized by a powder X-ray diffraction pattern comprising a powder X-ray diffraction peak at about 8.0° 2θ±0.2° 2θ.

In another embodiment, the DACT:methanol crystalline form is characterized by a powder X-ray diffraction pattern comprising powder X-ray diffraction peaks at about 6.0, 6.9, and 8.0° 2θ±0.2° 2θ.

In another aspect, the invention provides for a crystalline form of DACT and methylparaben. In one embodiment, the DACT:methylparaben crystalline form is a cocrystal.

In one embodiment, the crystalline form of DACT and methylparaben is a 1:1 DACT:methylparaben complex.

In another embodiment, the DACT:methylparaben crystalline form is characterized by a powder X-ray diffraction pattern comprising a powder X-ray diffraction peak at about 7.6° 2θ±0.2° 2θ.

In another embodiment, the DACT:methylparaben crystalline form is characterized by a powder X-ray diffraction pattern comprising a powder X-ray diffraction peak at about 8.7° 2θ±0.2° 2θ.

In another embodiment, the DACT:methylparaben crystalline form is characterized by a powder X-ray diffraction pattern comprising a powder X-ray diffraction peak at about 10.1° 2θ±0.2° 2θ.

In another embodiment, the DACT:methylparaben crystalline form is characterized by a powder X-ray diffraction pattern comprising a powder X-ray diffraction peak at about 12.3° 2θ±0.2° 2θ.

In another embodiment, the DACT:methylparaben crystalline form is characterized by a powder X-ray diffraction pattern comprising a powder X-ray diffraction peak at about 14.3° 2θ±0.2° 2θ.

In another embodiment, the DACT:methylparaben crystalline form is characterized by a powder X-ray diffraction pattern comprising a powder X-ray diffraction peak at about 15.9° 2θ±0.2° 2θ.

In another embodiment, the DACT:methylparaben crystalline form is characterized by a powder X-ray diffraction pattern comprising a powder X-ray diffraction peak at about 17.2° 2θ±0.2° 2θ.

In another embodiment, the DACT:methylparaben crystalline form is characterized by a powder X-ray diffraction pattern comprising powder X-ray diffraction peaks at about 7.6, 8.7, 10.1, 12.3, 14.3, 15.9, and 17.2° 2θ±0.2° 2θ.

In another aspect, the invention provides for a crystalline form of DACT and propylparaben. In one embodiment, the DACT:propylparaben molecular complex crystalline form could be a cocrystal.

In another embodiment, the DACT:propylparaben crystalline form is characterized by a powder X-ray diffraction pattern comprising a powder X-ray diffraction peak at about 7.5° 2θ±0.2° 2θ.

In another embodiment, the DACT:propylparaben crystalline form is characterized by a powder X-ray diffraction pattern comprising a powder X-ray diffraction peak at about 8.6° 2θ±0.2° 2θ.

In another embodiment, the DACT:propylparaben crystalline form is characterized by a powder X-ray diffraction pattern comprising a powder X-ray diffraction peak at about 10.1° 2θ±0.2° 2θ.

In another embodiment, the DACT:propylparaben crystalline form is characterized by a powder X-ray diffraction pattern comprising a powder X-ray diffraction peak at about 12.4° 2θ±0.2° 2θ.

In another embodiment, the DACT:propylparaben crystalline form is characterized by a powder X-ray diffraction pattern comprising a powder X-ray diffraction peak at about 14.3° 2θ±0.2° 2θ.

In another embodiment, the DACT:propylparaben crystalline form is characterized by a powder X-ray diffraction pattern comprising a powder X-ray diffraction peak at about 15.9° 2θ±0.2° 2θ.

In another embodiment, the DACT:propylparaben crystalline form is characterized by a powder X-ray diffraction pattern comprising a powder X-ray diffraction peak at about 16.1° 2θ±0.2° 2θ.

In another embodiment, the DACT:propylparaben crystalline form is characterized by a powder X-ray diffraction pattern comprising powder X-ray diffraction peaks at about 7.5, 8.6, 10.1, 12.4, 14.3, 15.9, and 16.1° 2θ±0.2° 2θ.

In another aspect, the invention provides for a crystalline form of DACT and diphenic acid. In one embodiment, the DACT:diphenic acid crystalline form could be a cocrystal.

In another embodiment, the DACT:diphenic acid crystalline form is characterized by a powder X-ray diffraction pattern comprising a powder X-ray diffraction peak at about 4.9° 2θ±0.2° 2θ.

In another embodiment, the DACT:diphenic acid crystalline form is characterized by a powder X-ray diffraction pattern comprising a powder X-ray diffraction peak at about 6.6° 2θ±0.2° 2θ.

In another embodiment, the DACT:diphenic acid crystalline form is characterized by a powder X-ray diffraction pattern comprising a powder X-ray diffraction peak at about 7.2° 2θ±0.2° 2θ.

In another embodiment, the DACT:diphenic acid crystalline form is characterized by a powder X-ray diffraction pattern comprising a powder X-ray diffraction peak at about 8.2° 2θ±0.2° 2θ.

In another embodiment, the DACT:diphenic acid crystalline form is characterized by a powder X-ray diffraction pattern comprising a powder X-ray diffraction peak at about 8.8° 2θ±0.2° 2θ.

In another embodiment, the DACT:diphenic acid crystalline form is characterized by a powder X-ray diffraction pattern comprising a powder X-ray diffraction peak at about 10.5° 2θ±0.2° 2θ.

In another embodiment, the DACT:diphenic acid crystalline form is characterized by a powder X-ray diffraction pattern comprising a powder X-ray diffraction peak at about 13.3° 2θ±0.2° 2θ.

In another embodiment, the DACT:diphenic acid crystalline form is characterized by a powder X-ray diffraction pattern comprising a powder X-ray diffraction peak at about 22.9° 2θ±0.2° 2θ.

In another embodiment, the DACT:diphenic acid crystalline form is characterized by a powder X-ray diffraction pattern comprising powder X-ray diffraction peaks at about 4.9, 6.6, 7.2, 8.2, 8.8, 10.5, 13.3, and 22.9° 2θ±0.2° 2θ.

In another aspect, the invention provides for a crystalline form of DACT and DL-cysteine.

In one embodiment, the DACT:DL-cysteine crystalline form could be a cocrystal.

In another embodiment, the DACT:DL-cysteine crystalline form is characterized by a powder X-ray diffraction pattern comprising a powder X-ray diffraction peak at about 15.0° 2θ±0.2° 2θ.

In another embodiment, the DACT:DL-cysteine crystalline form is characterized by a powder X-ray diffraction pattern comprising a powder X-ray diffraction peak at about 21.2° 2θ±0.2° 2θ.

In another embodiment, the DACT:DL-cysteine crystalline form is characterized by a powder X-ray diffraction pattern comprising a powder X-ray diffraction peak at about 22.5° 2θ±0.2° 2θ

In another embodiment, the DACT:DL-cysteine crystalline form is characterized by a powder X-ray diffraction pattern comprising a powder X-ray diffraction peak at about 30.0° 2θ±0.2° 2θ.

In another embodiment, the DACT:DL-cysteine crystalline form is characterized by a powder X-ray diffraction pattern comprising powder X-ray diffraction peaks at about 15.0, 21.2, 22.5, and 30.0° 2θ±0.2° 2θ.

The present invention includes complexes of DACT methanolate, methylparaben, propylparaben, diphenic acid, and DL-cysteine, which are capable of complexing in the solid-state, for example, through dry or solvent-drop grinding, heating or solvent evaporation of their solution in single or mixed solvent systems, slurry suspension, antisolvent, supercritical fluids or other techniques known to a person skilled in the art. Solvents and antisolvents used to make the crystalline forms include acetone, ethanol, methanol, ethylacetate (EtOAc), isopropanol (IPA), or isopropylacetate (IPAc), diethoxymethane (DEM), Toluene, BuOAc, N-methylpyrrolidone (NMP) and a heptane.

In one embodiment, the invention includes crystalline forms of DACT and methanol methylparaben, propylparaben, diphenic acid, and DL-cysteine, which are capable of complexing through solvent evaporation of their solution in single or mixed solvent systems, and slurry suspension.

In another embodiment, the invention includes crystalline forms of DACT with methylparaben, propylparaben, diphenic acid, and DL-cysteine, which have shown physical stability during storage under accelerated conditions of temperature of 40° C. and 75% relative humidity for at least one year.

In another embodiment, the complex of DACT with methylparaben, propylparaben, diphenic acid, and DL-cysteine have shown anti-cancer activity measured by the half-maximal inhibitory concentration ($IC_{50}$).

In another embodiment, the complex of DACT with methylparaben, propylparaben, diphenic acid have shown improved ($IC_{50}$) compared with the parent molecule (DACT) in treating sarcoma, skin, prostate, and pancreatic cancer.

In another embodiment, the complex of DACT with propylparaben has shown improved ($IC_{50}$) compared with the parent molecule (DACT) in treating lung cancer.

In another embodiment, the complex of DACT with methylparaben, propylparaben, diphenic acid, and DL-cysteine have shown anti-tumor activity measured by the half-maximal inhibitory concentration ($IC_{50}$).

In another embodiment, the complex of DACT with propylparaben has improved ($IC_{50}$) compared with the parent molecule (DACT) in treating tumoroids.

In another embodiment, the novel molecular complex DACT:propylparaben has reduced tumor sphere formation efficiency (SFE) compared with the parent molecule.

In another embodiment, the novel molecular complex DACT:propylparaben has reduced tumor spheres size (SSS) compared with that of the parent molecule.

In another aspect, the invention provides for a pharmaceutical composition comprising a molecular complex of DACT and methanol, methylparaben, propylparaben, diphenic acid or DL-cysteine. In one embodiment, the DACT:methanol molecular complex is a solvate. In another embodiment, the DACT:methylparaben molecular complex could be a cocrystal. In another embodiment, the DACT:propylparaben molecular complex could be a cocrystal. In another embodiment, the DACT:diphenic acid molecular complex could be a cocrystal. In another embodiment, the DACT:DL-cysteine molecular complex could be a cocrystal.

In some embodiments, a pharmaceutical composition of the present invention is delivered to a subject via intratumoral injection. "Intratumoral injection" is a route of administration by which a pharmaceutical composition, is delivered directly to the tumor via an injection device (e.g., needle and syringe). In some embodiments, a pharmaceutical composition of the present invention is delivered to a subject via a parenteral route, an enteral route, or a topical route.

Examples of parental routes include, without limitation, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (bolus or drip), intraventricular, intravesical and subcutaneous.

Enteral routes of administration include administration to the gastrointestinal tract via the mouth (oral), stomach (gastric), and rectum (rectal). Gastric administration typically involves the use of a tube through the nasal passage (NG tube) or a tube in the esophagus leading directly to the stomach (PEG tube). Rectal administration typically involves rectal suppositories.

Topical, including transdermal, routes of administration include administration to a body surface, such as skin or mucous membranes. Delivery vehicles of the present disclosure may be administered topically (or transdermally) via a cream, foam, gel, lotion or ointment, for example.

The pharmaceutical composition comprises a therapeutically effective amount of at least one of the novel molecular complexes of DACT according to the invention and at least one pharmaceutically acceptable excipient. The term "excipient" refers to a pharmaceutically acceptable, inactive substance used as a carrier for the pharmaceutically active ingredient(s) and includes antiadherents, binders, coatings, disintegrants, fillers, diluents, flavors, bulkants, colours, glidants, dispersing agents, wetting agents, lubricants, preservatives, sorbents, and sweeteners. The choice of excipient(s) will depend on factors such as the particular mode of administration and the nature of the dosage form. Solutions or suspensions used for intravenous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical formulation of the present invention may be in any pharmaceutical dosage form. The pharmaceutical formulation may be, for example, a tablet, capsule, nanoparticulate material, e.g., granulated particulate material or a powder, a lyophilized material for reconstitution, liquid suspension, injectable suspension or solution, suppository, or topical or transdermal preparation or patch. The pharmaceutical formulations generally contain about 1% to about 99% by weight of at least one novel molecular complex of DACT of the invention and 99% to 1% by weight of a suitable pharmaceutical excipient. In one embodiment, the dosage form is an oral dosage form. In another embodiment, the dosage form is a parenteral dosage form. In one embodiment, the pharmaceutical dosage form is a unit dose. The term "unit dose" refers to the amount of API administered to a patient in a single dose.

The novel molecular complexes of DACT are therapeutically useful for the treatment, prevention, and/or cure of a disease for which it is indicated, e.g., cancer. Accordingly, in another aspect, the invention also relates to methods of treatment using novel molecular complexes of DACT and, or a pharmaceutical formulation containing them. As used herein, the terms "treat," "treating," or "treatment" means to alleviate, reduce or abrogate one or more symptoms or characteristics of a disease and may be curative, palliative, prophylactic or slow the progression of the disease. The term "therapeutically effective amount" is intended to mean that amount of drug that will elicit a desired biological or pharmacological response, i.e., an amount sufficient to treat the disease. The term "patient" includes mammals, especially humans. In one embodiment, the patient is a warm-blooded mammal. In another embodiment, the patient is a human.

In another embodiment, the patient is a human male. In another embodiment, the patient is a human female.

In one embodiment, the invention provides for a method of treating pre-cancer or cancer comprising the step of administering to a cancer patient a therapeutically effective amount of a pharmaceutical composition of the present invention. The present invention further provides for a medicament comprising a pharmaceutical composition of the present invention for use in treating pre-cancer or cancer.

The dosage may vary depending upon the dosage form employed, sensitivity of the patient, and the route of administration. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In some embodiments, the cancer is selected from: Wilms' tumor, rhabdomyosarcoma, lung, breast, colon, rectal head and neck, brain, pancreatic, ovarian cancer (e.g., germ cell), gestational trophoblastic neoplasm, Ewing's sarcoma, metastatic testicular tumors (e.g., nonseminoatous), gestational trophoblastic neoplasm, locally recurrent or locoregional solid tumors (sarcomas, carcinomas and adenocarcinomas), acute myeloid leukemia (AML), multiple myeloma, prostate cancer, skin cancer, actinic keratosis, Bowen's disease, adjuvant cancer therapy or neoadjuvant cancer therapy. In a preferred embodiment, the cancer is skin cancer, actinic keratosis, or Bowen's disease. In a further embodiment, the skin cancer is selected from the group consisting of: basal cell carcinoma (BCC), squamous cell carcinoma (SCC), and melanoma. In another embodiment, the cancer is prostate cancer. In a further embodiment, the prostate cancer is selected from the group consisting of: acinar adenocarcinoma, ductal adenocarcinoma, transitional cell (or urothelial) cancer, squamous cell cancer, small cell prostate cancer, carcinoid, and sarcoma.

EXAMPLES

The techniques and approaches set forth in the present disclosure can further be used by the person of ordinary skill in the art to prepare variants thereof, the variants are considered to be part of the inventive disclosure.

Materials used to create the novel forms of the present inventions are commercially available and means to synthesize them as well known. DACT as a starting material used in all experiments in this disclosure was supplied by AdipoGen Life Sciences, CA, USA, with >98% purity by HPLC. All other pure chemicals (Analytical Grade) were supplied by Sigma-Aldrich and used without further purification. The cancer cell lines and culture growth media were purchased from ATCC (American Type Culture Collection, USA) company and subjected for testing anti-cancer potency or the half maximal inhibitory concentration (ICA. The incubator (Model 3120, Thermo Scientific, USA) was used throughout all experiments. Testing reagent used was CellTiter-Glo® 2.0 reagent (CTG, Promega Cat #G9243, USA). The plate luminescence reader (SynergyH4 Hybrid Reader, Biotek, USA) was implemented for all measurements.

Analytical techniques used to observe the crystalline forms include powder X-ray diffraction (PXRD) and Fourier transform infrared spectroscopy (FTIR). The particular methodology used in such analytical techniques herein should be viewed as illustrative, and not limiting in the context of data collection.

Powder X-Ray Diffraction (PXRD): All DACT novel molecular complex products were observed by a D-8 Bruker X-ray Powder Diffractometer using Cu Kα (λ=1.540562 Å), 40 kV, 40 mA. The data were collected over an angular range of 3° to 40° 2θ in continuous scan mode at room temperature using a step size of 0.05° 2θ and a scan speed of 6.17°/min.

FTIR analysis was performed on a Perkin Elmer Spectrum 100 FTIR spectrometer equipped with a solid-state ATR accessory.

The following examples illustrate the invention without intending to limit its scope.

Example 1: Preparation of DACT Methanolate Complex 50 mg of pure DACT was added to vial 1. A 1:1 mole physical mixture of DACT and Glucose was added to vial 2. Next, 2 mL of methanol was added to each glass vial and slurried for 16-24 hours. The solids were filtered off and air dried under ambient conditions for 16-24 hours under vacuum. The solids gathered from each vial after filtration were dried and stored in fresh screw cap vials for subsequent analysis. The materials were characterized by PXRD and FTIR corresponding to FIGS. 1 and 2, respectively.

Example 2: Preparation of DACT:Methylparaben Complex

DACT and methylparaben is stirred as a slurry for 16-24 hours in methanol at a 1:1 molar ratio of DACT:methylparaben in 1 mL per 50 mg of DACT. The solids are filtered off and air dried under ambient conditions for 16-24 hours under vacuum. This synthesis was scaled up to 100 mg of DACT input and to 2 g of DACT input. The solids gathered after filtration were dried and stored in a screw cap vials for subsequent analysis. All materials were characterized by PXRD and FTIR corresponding to FIGS. 3 and 4, respectively.

Example 3: Preparation of DACT:Propylparaben Complex

DACT and propylparaben is stirred as a slurry for 16-24 hours in methanol at a 1:1 ratio in 1 mL per 50 mg of DACT. The solids are filtered off and air dried under ambient conditions for 16-24 hours under vacuum. This synthesis was scaled up to 100 mg DACT input and to 2 g of DACT input. The material was stored for subsequent analysis. The material was characterized by PXRD and FTIR corresponding to FIGS. 5 and 6, respectively.

Example 4: Preparation of DACT:Diphenic Acid Complex 50 mg of DACT and 10 mg of diphenic acid (1:1 molar ratio) was stirred as a slurry in a closed vial with 1 mL of acetone. After 12-16 hours the mixture was dried at room temperature for another 12-16 hours. The material was stored for subsequent analysis. The material was characterized by PXRD and FTIR corresponding to FIGS. 7 and 8, respectively.

Example 5: Preparation of DACT:DL-Cysteine Complex 50 mg of DACT and 4.8 mg of DL-cysteine (1:1 molar ratio) was stirred as a slurry in a closed vial with 1 mL of acetone. After 12-16 hours the mixture was dried at room temperature for another 12-16 hours. The solids gathered after filtration were dried and stored in a screw cap vials for subsequent analysis. The material was characterized by PXRD and FTIR corresponding to FIGS. 9 and 10, respectively.

Example 6: Scale Up Experiments

This mg level synthesis was scaled-up to a gram level product to demonstrate scalability. Scale up experiments were carried out successfully for the novel forms to a gram level for DACT:methylparaben and propylparaben molecular complexes from 50 mg DACT input to 2000 mg input; a 40× scale up as shown in FIGS. 3 and 5 (top profile). DACT:diphenic acid was also successfully scaled up at least 10× as shown in FIG. 11.

Example 7: Accelerated Stability Studies

Stability studies of the DACT novel forms were conducted using accelerated conditions (75% humidity and 40° C.) of which are obvious to the artisan in the field, for more than one year. The novel solid forms were stressed under heat and humidity for a year and proved stable. Selected data of the novel complexes of DACT:methylparaben, propylparaben and diphenic acid proves this point. Samples pulled and analyzed at intervals of three months, six months and twelve months has demonstrated their physical form stability as suggested by the PXRD data of all the samples after one year of storage under such condition as shown in FIGS. 12, 13, and 14.

Example 8: $IC_{50}$ Studies

Cancer cell lines listed in Table 1 were subjected for testing anti-cancer potency or the half maximal inhibitory concentration ($IC_{50}$) of the D-Actinomycin (DACT) molecular complexes.

TABLE 1

Cell lines used for test on anti-cancer function of the DACT molecular complexes

| Cell Name | Catalog Name | Disease Type | Original Tissue |
|---|---|---|---|
| SK-ES-1 | ATCC ® HTB-86 | anaplastic osteosarcoma or Ewing's sarcoma | bone |
| U-2 OS | ATCC ® HTB-96 | osteosarcoma | bone |
| SK-MEL-5 | ATCC ® HTB-70 | malignant melanoma | skin: derived from metastatic axillary node |
| PC3 | ATCC ® CRL-1435 | adenocarcinoma | prostate; derived from metastatic site: bone |
| PANC-1 | ATCC ® CRL-1435 | epithelioid carcinoma | pancreas/duct |
| A549 | ATCC ® CCL-185 | carcinoma | lung |
| H460 | ATCC ® HTB-177 | carcinoma; large cell lung cancer | lung: pleural effusion |
| H1299 | ATCC ® CRL-5803 | carcinoma; non-small cell lung cancer | lung; derived from metastatic site: lymph node |

The SK-ES-1, U-2 OS, and SAOS-2 cells were cultured in a growth medium that is ATCC-formulated McCoy's 5a Medium Modified, Catalog No. 30-2007. The PC-3, PANC-1, SK-Mel-5, A549, H460, and H1299 were cultured in a growth medium that is ATCC-formulated Dulbecco's Modified Eagle's Medium (DMEM), Catalog No. 30-2002. The cells were seeded on 96-well microtiter plates with 3500 cells per well and cultured in an incubator (Model 3120, Thermo Scientific, USA) with a constant temperature at 37° C. and 5% carbon dioxide ($CO_2$) gas for 24 hours.

The new DACT-molecular complexes were made into a series with concentration of 200 nM to 40 nM, 8 nM, 1.6 nM, 0.32 nM, and 0.064 nM. 100 µl of each solution was then added into each well to bring out the final concentration of the drug treatment at 100 nM, 20 nM, 4 nM, 0.8 nM, 0.16 nM, or 0.032 nM, respectively.

The treated cells in the 96 well plate was then further cultured at the same conditions for 72 hours and then subjected for a final cell viability measurement. The measurement used a homogeneous method to determine the number of metabolically active cells presented in each of treatments. A testing reagent for the measurement is a mixture solution of the CellTiter-Glo® 2.0 reagent (CTG, Promega Cat #G9243, USA) and growth medium in 1:1 ratio in this respect.

The 96-well plate with the new molecular complex treated cells was taken out from incubator after the 72 hours of incubation, and the treatment solution in each well was removed using a multichannel pipette, and 100 µl of the testing reagent were added into each well. The plate was then placed on a plate shaker for 15 min. The plate was covered with a piece of aluminum foil to protect the CTG luminescence during the shaking time.

Then 90 µl of the 100 µl testing reagent were transferred into an opaque-walled 96-well plate for the CTG luminescence reading on a plate reader (SynergyH4 Hybrid Reader, Biotek, USA). The luminescence intensity of each treatment was positively correlated with the number of cells survived during the treatments.

All the treatment data was normalized by comparing with the control samples that had only growth medium without any molecular complexes. The half maximal inhibitory concentration ($IC_{50}$) data was calculated using the nonlinear regression model and dose-responses (inhibition) curve built in the software. Each of treatments was performed in three replications each time and repeated three times for validation. The $IC_{50}$ average volume (Avg) and standard deviation (STDV) were calculated based on the three replications.

All the DACT-molecular complexes with an outperformed or better potency comparing with the original compound DACT in inhabiting cancer cell growth have been listed in the Table 2.

TABLE 2

The half-maximal inhibitory concentration ($IC_{50}$) volume of each new DACT-molecular complexes on different cancer cells. $IC_{50}$ data were validated in three times (I, II, and III), and each time has three replications and presented here with their average (Avg.) and standard deviation (STDV).

| Monolayer Cell Culture Assay | | | $IC_{50}$ Test (I) | | $IC_{50}$ Test (II) | | $IC_{50}$ Test (III) | |
|---|---|---|---|---|---|---|---|---|
| Cancer Type | Cell Line | Compounds | Avg (nM) | STDV | Avg (nM) | STDV | Avg (nM) | STDV |
| Sarcoma | SK-ES-1 | DACT | 1.03 | 0.08 | 0.56 | 0.23 | 0.63 | 0.14 |
| | SK-ES-1 | DACT-methylparaben | 0.71 | 0.06 | 0.51 | 0.07 | 0.58 | 0.12 |
| | SK-ES-1 | DACT-propylparaben | 0.76 | 0.08 | 0.34 | 0.10 | 0.49 | 0.16 |
| Sarcoma | U-2 OS | DACT | 5.29 | 0.31 | 5.63 | 0.20 | 2.62 | 0.49 |
| | U-2 OS | DACT- diphenic Acid | 4.34 | 0.23 | 4.30 | 0.39 | 2.69 | 0.18 |
| | U-2 OS | DACT-methylparaben | 4.30 | 0.14 | 4.38 | 0.50 | 2.27 | 0.70 |
| | U-2 OS | DACT-propylparaben | 3.63 | 0.80 | 3.85 | 1.15 | 1.79 | 0.41 |
| Skin | SK-Mel-5 | DACT | 0.61 | 0.07 | 0.50 | 0.18 | 2.90 | 0.11 |
| | SK-Mel-5 | DACT-diphenic Acid | 0.42 | 0.07 | 0.32 | 0.13 | 2.30 | 0.42 |
| | SK-Mel-5 | DACT-methylparaben | 0.36 | 0.07 | 0.37 | 0.10 | 2.30 | 0.34 |
| | SK-Mel-5 | DACT-propylparaben | 0.39 | 0.18 | 0.27 | 0.08 | 2.59 | 0.10 |

TABLE 2-continued

The half-maximal inhibitory concentration (IC$_{50}$) volume of each new DACT-molecular complexes on different cancer cells. IC$_{50}$ data were validated in three times (I, II, and III), and each time has three replications and presented here with their average (Avg.) and standard deviation (STDV).

| Monolayer Cell Culture Assay | | | IC$_{50}$ Test (I) | | IC$_{50}$ Test (II) | | IC$_{50}$ Test (III) | |
|---|---|---|---|---|---|---|---|---|
| Cancer Type | Cell Line | Compounds | Avg (nM) | STDV | Avg (nM) | STDV | Avg (nM) | STDV |
| Prostate | PC-3 | DACT | 8.81 | 1.25 | 7.00 | 0.86 | 7.28 | 0.60 |
|  | PC-3 | DACT-diphenic Acid | 6.38 | 1.18 | 5.89 | 0.64 | 6.55 | 1.26 |
|  | PC-3 | DACT-methylparaben | 7.10 | 1.42 | 5.53 | 0.91 | 6.15 | 0.70 |
|  | PC-3 | DACT-propylparaben | 7.68 | 1.51 | 4.52 | 0.87 | 6.34 | 0.33 |
| Pancreatic | PANC-1 | DACT | 5.68 | 0.36 | 4.56 | 0.10 | 4.74 | 0.52 |
|  | PANC-1 | DACT-diphenic Acid | 5.31 | 1.56 | 3.25 | 0.43 | 3.83 | 0.21 |
|  | PANC-1 | DACT-methylparaben | 4.15 | 0.69 | 2.66 | 0.75 | 3.48 | 0.80 |
|  | PANC-1 | DACT-propylparaben | 4.61 | 0.68 | 1.71 | 0.58 | 3.29 | 0.64 |
| Lung | A549 | DACT | 1.64 | 0.17 | 1.85 | 0.02 | 1.64 | 0.06 |
|  | A549 | DACT-propylparaben | 1.39 | 0.21 | 1.74 | 0.20 | 1.63 | 0.45 |
| Lung | H460 | DACT | 0.35 | 0.03 | 0.35 | 0.02 | 0.35 | 0.01 |
|  | H460 | DACT-propylparaben | 0.21 | 0.07 | 0.30 | 0.01 | 0.15 | 0.05 |
| Lung | H1299 | DACT | 1.78 | 0.08 | 1.15 | 0.07 | 1.28 | 0.01 |
|  | H1299 | DACT-propylparaben | 1.48 | 0.34 | 0.96 | 0.16 | 1.05 | 0.11 |

Example 9: Tumor Sphere Formation Studies

Cancer stem cells (CSCs) are defined as a small subset of cells within a tumor with the ability to self-renew and often drive tumor progression and recurrence after chemotherapy treatment (Xiaochen Zhou, et al. 2015. A Reliable Parameter to Standardize the Scoring of Stem Cell Spheres. PLOS One 10(5); e0127348). It is important to study the responses of cancer stem cells or the tumors treated with the new molecular complexes. We have assessed cancer stem cells (CSCs) growth using tumor sphere formation assay, which involves culturing cancer cells in low attachment plates in serum free media. Sphere size and diameter was measured using ImageJ software and statistical analysis was performed using Graph Pad Prism Software.

The stem cell culture medium is prepared for 500 ml (250 ml of Dulbecco's Modified Eagle Medium (DMEM) (ATCC® 30-2002) plus 250 ml of F-12K medium (ATCC® 30-2004)) using 20 ng/ml epidermal growth factor, 10 ng/ml basic fibroblast growth factor, 5 µg/ml insulin and 0.4% Bovine Serum Albumin. All preparation methods known to the person skilled in the art.

The cancer cell line used in this study was human sarcoma cell line SK-ES-1. The cells were seeded in a density of 200 per well per 200 µl in a 96-well Ultra-Low Attachment plate (Corning, Cat #3474, USA), this plate is specially treated for stem cell growth or tumor culture. On the day 1 of seeding, 100 µl of cell solution was added into the plate. On the day 2, 100 µl of treatment solution which is the stem cell culture medium mixed containing DACT molecular complex; DACT:propylparaben in this case, and were gently added into the treatment wells. The DACT molecular concentrations prepared were 200 nM, 40 nM, 8 nM, 1.6 nM, 0.32 nM, and 0.064 nM. 100 µl of each solution was then added into each well to bring out the final concentration at 100 nM, 20 nM, 4 nM, 0.8 nM, 0.16 nM, or 0.032 nM, respectively.

On the day 6 of seeding, 10 µl of NucBlue Live Cell Stain ReadyProbes (Invitrogen Cat #R37605, USA) were added into each well for staining to visualize the live cells under the blue fluorescent light. The staining took place in an incubator for 2-3 hours at 37° C. Then the plate was brought to the Keyence imaging device (Keyence America, All-in-One Fluorescence Microscope BZ-X800, USA) for image scanning. The sphere images in each well were saved in "Tiff" file for data analysis. The ImageJ software (National Institutes of Health, USA) and its "particle analysis" function were used to identifying and measuring numbers and diameters of spheres by each treatment. The data only included the spheres with diameter over 50 µm.

The sum of sphere image area of every individual sphere, with diameter over 50 µm, in each well was calculated. Each treatment was performed in triplicates, and the average volume and standard deviation (STDV) in error bar were expressed in FIG. 15. The data suggests that there was a noticeable reduction in sphere area in wells treated with the DACT molecular complex compared with that of the pure parent molecule DACT. The sphere image area was calculated based on the sum area of spheres with diameter over 50 µm in each treatment well, and significance was declared at P<0.05 for the bars indicated by *, and P<0.001 by **. This was verified by the sphere images shown in FIG. 16. The invention is thus also directed to a method of eliminating or reducing cancer stem cells, comprising the administration to a patient in need thereof, a therapeutically effective amount of a pharmaceutical composition comprising the crystalline forms of actinomycin D of the invention.

What is claimed:

1. A crystalline form selected from the group consisting of: actinomycin D:methanol, actinomycin D:methylparaben, actinomycin D:propylparaben, actinomycin D:diphenicacid, and actinomycin D:DL-cysteine, wherein:
   the actinomycin D:methanol crystalline form is characterized by a powder X-ray diffraction pattern comprisingpowderX-ray diffraction peaks at about: 6.0, 6.9, and 8.0° 2θ±0.2° 2θ;
   the actinomycin D:methylparaben crystalline form is characterized by a powder X-ray diffraction pattern comprising three or more powder X-ray diffraction peaks selected from the group consisting of about: 7.6, 8.7, 10.1, 12.3, 14.3, 15.9, and 17.2° 2θ±0.2° 2θ;
   the actinomycin D:propylparaben crystalline form is characterized by a powder X-ray diffraction pattern comprising three or more powder X-ray diffraction peaks selected from the group consisting of about: 7.5, 8.6, 10.1, 12.4, 14.3, 15.9, and 16.1° 2θ±0.2° 2θ;
   the actinomycin D:diphenicacid crystalline form is characterized by a powder X-ray diffraction pattern comprising three or more powder X-ray diffraction peaks selected from the group consisting of about: 4.9, 6.6, 7.2, 8.2, 8.8, 10.5, 13.3, and 22.9° 2θ±0.2° 2θ; and the actinomycin D:DL-cysteine crystalline form is characterized by a powder X-ray diffraction pattern comprising three or more powder X-ray diffraction peaks selected from the group consisting of about: 15.0, 21.2, 22.5, and 30.0° 2θ±0.2° 2θ.

2. The crystalline form of claim 1, wherein the crystalline form is actinomycin D:methanol.

3. The crystalline form of claim 1, wherein the crystalline form is actinomycin D:methylparaben.

4. The crystalline form of claim 1, wherein the crystalline form is actinomycin D:propylparaben.

5. The crystalline form of claim 1, wherein the crystalline form is actinomycin D:diphenic acid.

6. The crystalline form of claim 1, wherein the crystalline form is actinomycin D:DL-cysteine.

7. A composition comprising the crystalline form of claim 1.

8. A pharmaceutical composition comprising the crystalline form of claim 1 and at least one pharmaceutically acceptable excipient.

9. The pharmaceutical composition of claim 8, wherein the pharmaceutical composition is an oral dosage form, a topical dosage form, or an injectable dosage form.

10. The pharmaceutical composition of claim 8, wherein the pharmaceutical composition is a solid dosage form for reconstitution in at least one medium.

11. The pharmaceutical composition of claim 10, wherein the medium is an aqueous or oil based liquid.

12. The pharmaceutical composition of claim 8, wherein the pharmaceutical composition is a unit dose.

13. A method of treating cancer for which actinomycin D is indicated, the method comprisingthe step of administering to a patient in need thereof, a therapeutically effe ctive amount of a pharmaceutical composition of claim 8, wherein the cancer is selected from the group consisting of: sarcoma, skin, prostate, pancreatic, and lung cancer.

14. The method of claim 13, wherein the crystalline forms of actinomycin D:methanol, actinomycin D:methylparaben, actinomycin D:propylparaben, actinomycin D:diphenic acid, or actinomycin D:DL-cysteine have improved (IC50) compared with that of actinomycin D alone.

15. The method of claim 13, wherein the crystalline form is actinomycin D:propylparaben and the cancer is lung cancer.

16. A method of eliminatingcancer stem cells usingactinomycin D novel forms, the method comprisingthe step of administeringto a patient in need thereof, a therapeutically effective amount of a pharmaceutical composition of claim 8, wherein the cancer is selected from the group consistingof: sarcoma, skin, prostate, pancreatic, and lung cancer.

17. The method of claim 16, wherein the crystalline forms of actinomycin D:methanol, actinomycin D:methylparaben, actinomycin D:propylparaben, actinomycin D:diphenic acid, or actinomycin D:DL-cysteine have improved (IC50) compared with that of actinomycin D alone.

18. The method of claim 16, wherein the crystalline form is actinomycin D:propylparaben and the cancer is lung cancer.

19. A method of making the crystalline form of claim 1, comprising the steps of: combining actinomycin D and a former selected from the group consisting of: methanol, methylparaben, propylparaben, diphenic acid, or DL-cysteine; and forming crystals of the actinomycin D and the former.

20. The method of claim 19, wherein the method comprises the step of combining the actinomycin D and the former with a solvent.

* * * * *